US011632919B2

(12) United States Patent
Bussell

(10) Patent No.: US 11,632,919 B2
(45) Date of Patent: Apr. 25, 2023

(54) SUBMERSIBLE AQUATIC ALGAE CULTIVATION SYSTEM

(76) Inventor: Stuart Bussell, Carlsbad, CA (US)

( * ) Notice: Subject to any disclaimer, the term of this patent is extended or adjusted under 35 U.S.C. 154(b) by 620 days.

(21) Appl. No.: 12/812,532

(22) PCT Filed: Jan. 23, 2009

(86) PCT No.: PCT/US2009/000455
§ 371 (c)(1),
(2), (4) Date: Jul. 12, 2010

(87) PCT Pub. No.: WO2009/094196
PCT Pub. Date: Jul. 30, 2009

(65) Prior Publication Data
US 2010/0287829 A1 Nov. 18, 2010

Related U.S. Application Data

(60) Provisional application No. 61/011,932, filed on Jan. 23, 2008.

(51) Int. Cl.
*A01G 33/00* (2006.01)
*C12M 1/09* (2006.01)
*C12M 1/00* (2006.01)

(52) U.S. Cl.
CPC .............. *A01G 33/00* (2013.01); *C12M 21/02* (2013.01); *C12M 23/18* (2013.01); *C12M 23/56* (2013.01); *Y02A 40/80* (2018.01)

(58) Field of Classification Search
CPC ..... A01K 61/007; A01G 33/00; C12M 21/02; C12M 23/18; C12M 23/56

USPC ............................................... 47/1.4; 119/223
See application file for complete search history.

(56) References Cited

U.S. PATENT DOCUMENTS

| | | | | |
|---|---|---|---|---|
| 3,402,506 A | * | 9/1968 | Renfro | 47/59 R |
| 3,653,358 A | * | 4/1972 | Fremont | 119/223 |
| 3,698,359 A | * | 10/1972 | Fremont | 119/223 |
| 3,955,317 A | | 5/1976 | Gudin | |

(Continued)

FOREIGN PATENT DOCUMENTS

| | | | | |
|---|---|---|---|---|
| EP | 0310522 A1 | 4/1989 | | |
| GB | 2221824 A | * | 2/1990 | ........... A01K 61/007 |

(Continued)

OTHER PUBLICATIONS

Sheehan, J., T. Dunahay, J. Benemann, and P. Roessler. 1998. A look back at the U.S. department of Energy's aquatic species program: Biodiesel from algae. NREL, TP-580-24190.

(Continued)

*Primary Examiner* — Son T Nguyen
(74) *Attorney, Agent, or Firm* — James G. Passe; Passe Intellectual Property, LLC

(57) ABSTRACT

Floating ponds for the cultivation of algae are disclosed. The floating ponds consist of a buoyant framework, a liner, a culture, and a mooring system. Submersible floating ponds are disclosed with a buoyant framework built from tubes that may be filled or partially filled with, for example, air, or water, or the surrounding water, or the culture, and thereby the present invention provides a framework in which the buoyancy may be modulated. Use of submerging lines and spools are disclosed to control the orientation and depth of the floating pond during submersion.

42 Claims, 11 Drawing Sheets

(56) References Cited

U.S. PATENT DOCUMENTS

| | | | | |
|---|---|---|---|---|
| 4,086,874 A | * | 5/1978 | Sterner | A01K 73/12 |
| | | | | 119/223 |
| 4,244,323 A | * | 1/1981 | Morimura | A01K 61/60 |
| | | | | 119/223 |
| 4,487,588 A | | 12/1984 | Lewis, III et al. | |
| 4,536,988 A | | 8/1985 | Hogen | |
| 4,695,411 A | | 9/1987 | Stern et al. | |
| 4,876,985 A | * | 10/1989 | Marcum et al. | 119/240 |
| 5,250,427 A | | 10/1993 | Weaver et al. | |
| 5,270,175 A | | 12/1993 | Moll | |
| 5,309,672 A | * | 5/1994 | Spencer | A01G 33/00 |
| | | | | 119/208 |
| 5,329,719 A | * | 7/1994 | Holyoak | 43/6.5 |
| 5,338,471 A | | 8/1994 | Lal | |
| 5,354,878 A | | 10/1994 | Connemann et al. | |
| 5,528,856 A | * | 6/1996 | Smith | C02F 3/327 |
| | | | | 47/1.4 |
| 5,661,017 A | | 8/1997 | Dunahay et al. | |
| 5,730,029 A | | 3/1998 | Stoldt et al. | |
| 5,910,254 A | | 6/1999 | Guelcher et al. | |
| 6,000,551 A | | 12/1999 | Kanel et al. | |
| 6,156,561 A | | 12/2000 | Kodo et al. | |
| 6,481,378 B1 | * | 11/2002 | Zemach | 119/223 |
| 6,524,486 B2 | | 2/2003 | Borodyanski et al. | |
| 6,538,146 B2 | | 3/2003 | Turek | |
| 6,854,408 B2 | | 2/2005 | De Baan | |
| 6,960,672 B2 | | 11/2005 | Nakayama et al. | |
| 6,986,323 B2 | | 6/2006 | Ayers | |
| 7,244,155 B1 | | 7/2007 | Nye et al. | |
| 2002/0079270 A1 | | 6/2002 | Borodyanski et al. | |
| 2004/0121447 A1 | | 6/2004 | Fournier | |
| 2007/0124995 A1 | * | 6/2007 | Kania et al. | 47/59 R |
| 2008/0029041 A1 | * | 2/2008 | McRobert | A01K 61/60 |
| | | | | 119/223 |
| 2008/0276532 A1 | * | 11/2008 | Kania | A01G 9/00 |
| | | | | 47/59 R |
| 2009/0134091 A1 | * | 5/2009 | Stephens | A01G 33/00 |
| | | | | 210/602 |

FOREIGN PATENT DOCUMENTS

| | | | | |
|---|---|---|---|---|
| JP | 2002176879 A | * | 6/2002 | A01K 61/60 |
| KR | 1020070009690 A | | 1/2007 | |

OTHER PUBLICATIONS

Jones, I. S. F., and D. Otaegui. 1997. Photosynthetic greenhouse gas mitigation by ocean nourishment. Energy Conversion and Management 38, : S367-72.
Komori, S., T. Shimada, and Y. Murakami. 1995. Laboratory estimation of $CO_2$ transfer velocity across the air-sea interface. In Biogeochemical processes and ocean flux in the western pacific., eds. H. Sakai, Y. Nozaki, 69-81. Tokyo TERRAPUB.
Canada, R., Jr., and D. May. 1985. Mooring developments and design philosophy at the national data buoy center. Oceans. vol. 17.
Grosenbaugh, M. A. 1995. Designing oceanographic surface moorings to withstand fatigue. Journal of Atmospheric and Oceanic Technology 12, (5) (Oct.): 1101-10.
Grosenbaugh, M. A. 1996. On the dynamics of oceanographic surface moorings. Ocean Engineering 23, (1) (Jan.) 7-25.
Dote, Y., S. Inoue, T. Ogi, and S. Yokoyama. 1996 Studies on the direct liquefaction of protein-contained biomass: The distribution of nitrogen in the products. Biomass & Bioenergy 11, (6): 491-8.
Matsui, T. O., A. Nishihara, C. Ueda, M. Ohtsuki, N. O. Ikenaga, and T. Suzuki. 1997. Liquefaction of micro-algae with iron catalyst. Fuel 76, (11) (Sep.): 1043-8.
Minowa, T., and S. Sawayama. 1999. A novel microalgal system for energy production with nitrogen cycling. Fuel 78, (10) (Aug.): 1213-5.
Sanford et al., 1993, Meth. Enzymol. 217:483-509.
Dunahay et al., 1997, Meth. Molec. Biol. 62:503-9.
Smith et al., Northwest Science, 1968, 42:165-171.
Moulton et al., Hydrobiologia 1990, 204/205:401-408.
Borowitzka et al., Bulletin of Marine Science, 1990, 47:244-252.
J. Am. Oil Soc. 61 :343, 1984.
Dote et al., Recovery of liquid fuel from hydrocarbon-rich microalgae by thermochemical liquefaction, 1994, Fuel 73:12.
Ginzburg, 1993, Renewable Energy 3:249-52.
Benemann and Oswald, Systems and economic Analysis of Microalgae Ponds for Conversion of $CO_2$ to Biomass, 1996, DOE/PC/93204-T5.
Examination Report from Indian Corresponding Application No. 5951/DELNP/2010.
Heussler et al., Ecological balance of algal cultures in arid climates: Major results of the Peruvian-German Microalgae Project at Trujillo, Dec. 1978.
Rose et al., Cross-Flow Utrafiltration Used in Algal High Rate Oxidation Pond Treatment of Saline Organic Effluents with the Recovery of Products of Value, vol. 25, No. 10pp. 319-327, 1992.

* cited by examiner

SUBMERSIBLE AQUATIC ALGAE CULTIVATION SYSTEM

CROSS REFERENCE TO RELATED APPLICATIONS

This application claims priority to U.S. provisional application number U.S. 61/011,932, filed Jan. 23, 2008, naming Stuart Bussell as inventor.

FIELD OF THE INVENTION

This invention relates most generally to a cultivation system. The invention relates more specifically to a floating pond and a method for the cultivation of algae.

BACKGROUND OF THE INVENTION

The world is experiencing increasing demand for energy, food, and water at a time of uncertain supplies. Large populations in countries like India and China are undergoing industrialization, with the concomitant intensification of per capita resource utilization. This intensification adds to the stretching of supplies and exacerbates environmental consequences.

Continued future availability of energy is questionable at a time of intense use of non-renewable fossil fuels. Known oil reserves are predicted to continue to decline, and global warming, caused in part by increased concentrations of atmospheric $CO_2$ as a result of burning fossil fuels, will only accelerate with their continued use. In addition, increased worldwide food demand stretches already thin supplies. Fresh water for producing crops is scarce in many parts of the world, and natural food stocks like oceanic fisheries are being harvested faster than they can replenish themselves. As a result, new sources of affordable energy and food are needed.

Fossil fuels have been a preferred source of energy worldwide for many reasons. Compared to alternatives, they are relatively low cost. They have a high energy density, requiring a small mass to produce a given amount of work. This makes them useful for large power plants as well as for individual use in cars and homes. The success of fossil fuels has lead to huge worldwide investments, including ones for exploration, drilling, transportation, refining, distribution, and utilization. As a result, an affordable renewable source is desired that shares at least some of the infrastructure and advantages of fossil fuels while avoiding or reversing their environmental impact.

Biofuels are seen by many as a renewable replacement, or supplement, for fossil fuels, but problems need to be overcome. Examples of biofuels include production of ethanol from corn or sugar cane, production of natural gas and biodiesel from agricultural crops or waste, and production of same from algae. However, so far none have been able to compete on a cost basis with fossil fuels. In addition, use of agricultural crops for production of biofuels introduces the opportunity cost of diverting these resources from food production.

Large scale use of algae has been proposed for decades as a potential supply of food and fuel (Richmond, 1986). Some of the appeal of algae is their fast growth rates compared to conventional terrestrial crops and simple nutritional requirements. They do not require the use of arable land and varieties are available that are adapted to fresh and salt water.

Despite these advantages, however, algae have failed to become an appreciable source of energy or food. As demonstrated by an extensive multi-decade program by the United States National Renewable Energy Laboratory to develop algae for biofuels (Sheehan, 1998), a major problem with algae is the inability to produce large amounts of it at competitive prices.

Algae have failed to compete on a large scale with fossil fuels and traditional farming of plants for a number of reasons:

1. since algae are aquatic, they can require large amounts of costly water,
2. the costs of installing and maintaining an algae pond can be prohibitive,
3. operational costs, including $CO_2$ supplies and energy for mixing to operate high productivity ponds, can be prohibitive, and
4. harvesting the algae from the ponds can be costly.

In order to make the cultivation of algae cost effective compared to conventional crops, most or all of the factors listed above disfavoring algae must be mitigated or reversed. It is expected that reversal of the first three factors will lead to large supplies of algal biomass and innovations in harvesting and other downstream activities like conversion of biomass to fuel.

Past systems built to cultivate algae cost effectively can be categorized into three distinct groups, open systems, closed systems, and hybrid systems, and all are located on land. The systems are characterized by whether the cultures are exposed to the surrounding environment. Open systems are exposed, closed systems are not, and hybrid systems attempt to combine the best qualities of each.

A typical open system is the racetrack pond. It derives its name from its resemblance to a horse racetrack. The pond depth is typically several feet deep, and the culture is usually circulated around the track by using a powered paddle wheel. The paddle wheel provides mixing to the pond. Expenses for nutrients, including $CO_2$ gas, water, and power are some of the major operating costs of an open system of this design. Substantial fixed costs, like the installation of the pond and the cost of the land underneath it, also contribute to making the costs of operating open systems prohibitive compared to conventional farms. Referring to the list of cost factors above, open systems are prone to all four and represent the base case for the following comparisons.

There are many types of closed systems that have been developed for the cultivation of algae in attempts to improve yields and reduce costs. The logic behind these attempts is that by using a well controlled system that is isolated from environmental contamination, high yielding species of algae can be cultivated without interference from others, and conditions for the culture can be optimized for highest yields. Comparing the cost factors of closed systems to racetrack type open systems, they suffer from the same ones, but the balance between them is shifted. Closed systems have the potential to save water because they suffer from less evaporation during cultivation. However, the evaporation in open systems provides a mechanism to cool the pond, and cost savings from using less water can easily be surpassed by more energy needed to cool the culture. Because closed systems are more highly engineered, installation and maintenance costs of closed systems tend to be much higher than those for racetrack type open systems. Finally, while yields can be higher for closed systems, the operational costs tend to be higher, mitigating or even reversing any potential benefits from the higher yields.

Hybrid systems attempt to mix the best qualities of open and closed systems in order to achieve economic competitiveness. Usually, small closed systems grow a preferred algae species which then seed a large open system. The higher fixed and operational costs of the closed system are kept to a minimum by keeping its relative size small, while the risk of environmental exposure of the open system is minimized by seeding it with sufficient amounts of algae from the closed system so that the preferred species dominates the pond. The problem with large scale use of hybrid systems is that they don't address the basic four cost disadvantages of open and closed systems listed above relative to conventional farming; they merely minimize these costs between themselves. They fail to alter the basic cost advantages of conventional farms for the large scale production of biomass over existing designs for algae ponds. While hybrid systems are capable of producing specialty products at the cheapest price, they have been unable to directly compete with conventional farms.

Turning to aquatic systems, ocean seeding has been tested to induce algae blooms in normally fallow areas of the ocean as a potential mitigator to global warming (Jones, 1997). The goal is to turn large areas into net $CO_2$ absorbers. Possible economic gain is possible if a system of carbon emission offsets is in place whereby emissions of $CO_2$ in one location are offset by paying for offsets generated by absorption in another. Harvesting of the algae, in this case, is impractical because of the dispersion of the algae through large volumes at low concentrations.

The absence of any large scale algae cultivation system competing directly with conventional plant crops is the best proof that a cost effective algae system has yet to be developed. If it had, it would quickly complement or replace existing plant farming practices.

SUMMARY OF THE INVENTION

In its most general form, the current invention is a floating pond that can convert large areas of water into acreage for cultivating algae. It reduces the contributing costs of algae cultivation systems, some to almost insignificant levels. It does this in several cohesive ways.

In one embodiment, the present invention provides for an aquatic algae cultivation system, or floating pond. Having an aquatic-based system essentially eliminates the cost of water and eliminates the cost of land. The cultivation system of the present invention can be set up in an ocean or any other body of water large enough to contain it. Surrounding water is used to fill the pond and, such as in the case of sea water, supplies many nutrients. Use of an aquatic floating pond avoids competition with other uses for land. Furthermore, it avoids costs associated with terrestrial locations like site leveling.

In another embodiment, the aquatic algae cultivation system is constructed from low weight bearing components, e.g. piping and plastic liner. Because the system is suspended in water, it has the advantage that it can be constructed from low weight bearing components for the framework and less expensive components, e.g. plastic liner, to separate the pond from surrounding water. Exposure of components to floating or submerged conditions limits the weight and stresses to which they are exposed, thereby enabling use of materials and geometries unsuitable for terrestrial installation. Use of tubes and piping for the framework of the floating pond simplifies construction and scaling to large ponds. In some embodiments, the system is submersible, thereby protecting it during violent surface conditions. This enables it to avoid the costs of constructing it to survive worst case conditions. In this way, installation and maintenance costs are kept to a minimum. In some embodiments of the invention, the overall system is constructed of low cost repeating ponds that can be coupled together to give a virtually unlimited size farm.

In another embodiment, the present invention provides an algae cultivation system that takes into account conditions, for example, geographic conditions, and the algae cultivation system is constructed to utilize the natural mixing of wind and waves to achieve high $CO_2$ transfer rates with the atmosphere and good mixing without the need for additional $CO_2$ and/or energy input. It does this by using a flexible liner for the pool bottom and, in some embodiments, the geometry and orientation of the pond are arranged to maximize wind and wave mixing as well as creating a current within the pond. For example, long rectangular ponds oriented with their long dimension parallel to the wind will experience significant mixing and current flow that can be used to advantage. Oceanic winds, such as those in equatorial regions, blow predictably in one direction, in this case East to West or vice versa. The mixing from such winds, and the waves they generate, causes gas exchange rates to increase 10-20 fold compared to more quiescent conditions (Komori, 1995). Data on ocean winds and currents, as collated by NASA's Physical Oceanography Program, can be used to choose the best locations to situate the cultivation systems of the present invention. This information may be obtained on the internet, and there are resources such as "Ocean Motion and Surface Currents" that can give up-to-date information and also provide a research tool for determining the ideal placements for a floating pond. Sloped terrestrial algae ponds operating under similar conditions, but requiring $CO_2$ sparging because of calmer environmental conditions, generate very high dry algae yields of 54 g/m²/day (Huessler, 1978).

Another embodiment of the present invention provides an algae cultivation system with a framework incorporating tubes that also function as ballast tanks and conduits to pump in nutrients and pump out the culture for harvest. In this way, operational costs, including harvesting, are kept to a minimum. In addition, when the system is submerged, ballast tanks are filled with the culture so that it can be used to quickly initiate growth and harvesting in the pond following submersion and surfacing processes.

The above elements, when combined as described herein, potentiate large scale algae farming. In this way, huge areas of previously unusable water surface can be utilized for the production of biomass. Benefits for such an invention include reduction of $CO_2$ in the atmosphere to reduce the severity of global warming, production of low cost food, production of biofuels, and production of raw materials for organic chemical synthesis. Other objects, advantages and novel features of the present invention will become apparent from the following detailed description of the invention when considered in conjunction with the accompanying drawings.

BRIEF DESCRIPTION OF THE DRAWINGS

FIG. 5b is a more detailed perspective view diagram of a section of the rectangular floating pond from the drawing in FIG. 5a, and FIG. 5c is an even more detailed perspective view diagram of a transverse member of the rectangular floating pond from the drawing in FIG. 5a.

DETAILED DESCRIPTION OF THE DRAWINGS

Non-limiting examples of the features and advantages of the present invention are illustrated in detail in the accompanying drawings, wherein like reference numbers refer to like elements throughout the drawings. Although the drawings are intended to illustrate the present invention, the drawings are not necessarily drawn to scale.

Figure 1:
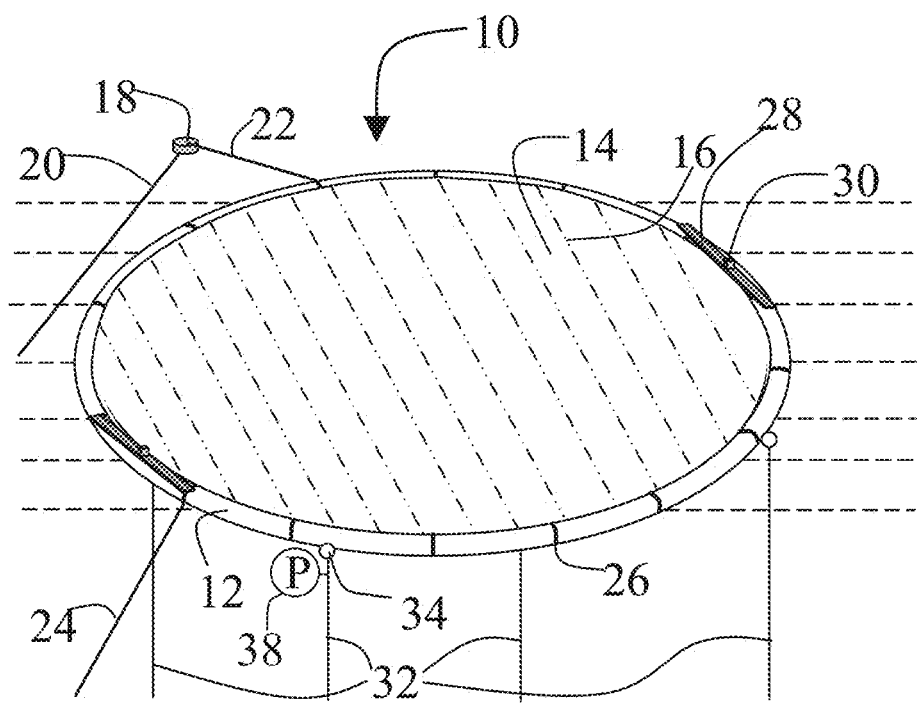
FIG. 1 is a perspective view diagram of a cultivation system of the present invention.

FIG. 1 is a drawing of a perspective view of a circular floating pond 10 with the four required subcomponents of the invention including a buoyant framework 12, a liner 14 attached to the framework, a culture 16, and a mooring system, in this case consisting of both a mooring line 24 connecting the framework to the subsurface and a mooring line 22 connecting the framework to an anchor buoy 18. The anchor buoy is attached to the subsurface with an additional mooring line 20. Mooring lines attaching to subsurfaces of various depths are well described (Canada, 1985; Grosenbaugh 1995; Grosenbaugh 1996). Because the floating pond 10 is circular, the framework 12 is constructed from a single continuous framework member. Circumferential bands 26 are placed on the framework 12 to introduce mechanical elements to which platforms 28 are mounted with equipment 30 on top. Equipment can include pumps, winches, sampling devices, sensors, beacons, two-way radios, buoys, rafts, boats, supplies, tanks, etc.

Figure 2A:
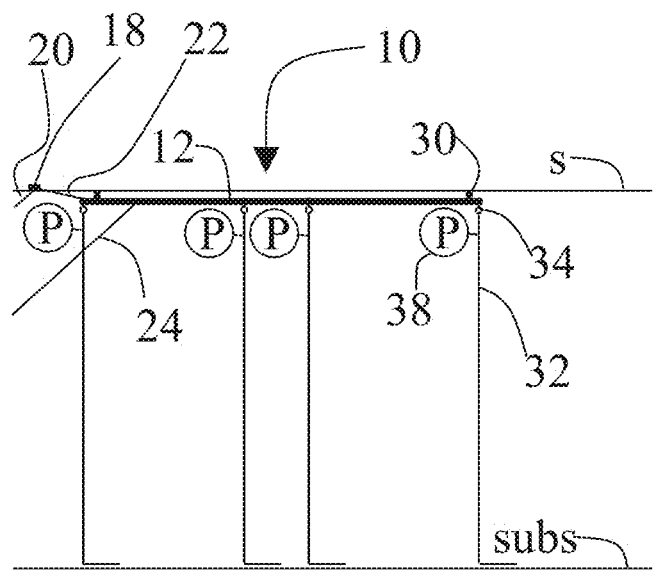
FIGS. 2a and 2b are elevational view diagrams illustrating a non-limiting submersion process of a cultivation system of the present invention.
Figure 2B:
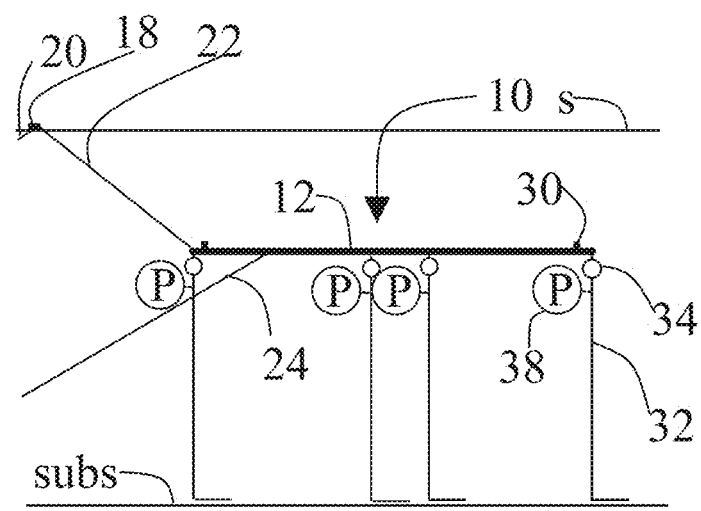

FIGS. 2a and 2b provide elevational views to help illustrate an example of how a system of the present invention works. In FIG. 2a, the buoyant framework 12 may be filled or partially filled with, for example, air, or water, or the surrounding water, or the culture, and thereby the present invention provides a framework 12 in which the buoyancy may be modulated. Valves and systems to fill the framework with liquids and air are well know to those of ordinary skill in the art and are not shown in the figure. The floating pond 10 is then submerged below the surface s by increasing the weight of at least one of the submerging lines 32 by adjusting its spool or winch 34 until the net weight of the submerging lines exceeds the buoyant forces of the floating pond 10. As the floating pond 10 sinks, the submerging lines 32 coil on the subsurface subs, decreasing their net weight until an equilibrium is established at a given depth for the floating pond, as shown in FIG. 2b. The arrangement of the submerging lines 32 is such that they can be used to set the depth and orientation of the floating pond 10. Depth gauges and level gauges, such as pressure sensor 38, can be used to guide this. Use of the submerging lines 32 and winches 34 establishes a stable submersion system. If perturbations raise the level of the pond or change its orientation, more of the submerging lines 32 are lifted off the subsurface, increasing their net weight on the floating pond 10 and thus returning it towards to its original position. Likewise, if perturbations lower the level of the pond, more of the submerging lines 32 are added to the subsurface, reducing their net weight on the floating pond 10 and again returning it towards its original position.

Figure 3A:
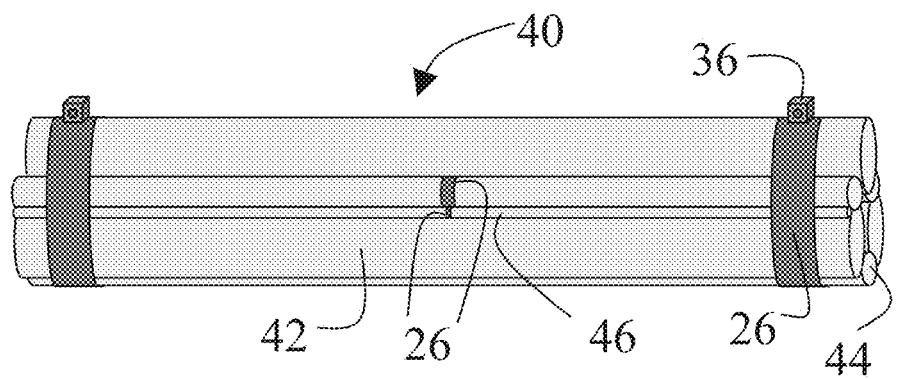
FIG. 3a is a perspective view diagram of a framework member constructed from constitutive components.
Figure 3B:
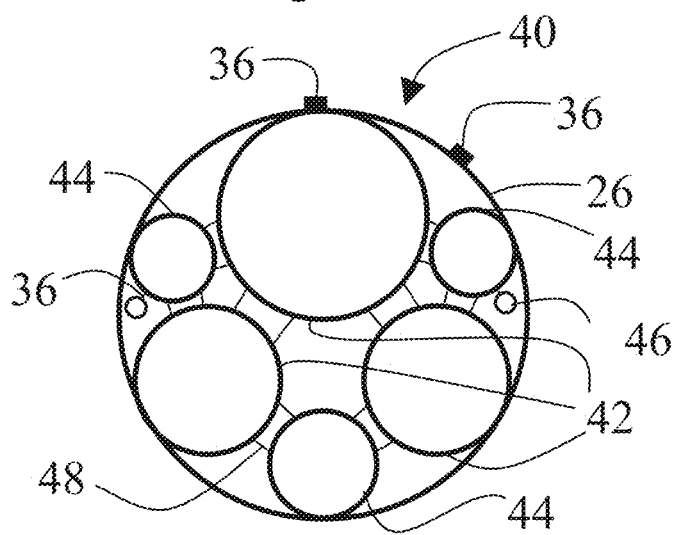
FIG. 3b is an elevational cross-sectional view diagram of the same framework member from the drawing in FIG. 3a, and FIG. 3c is a perspective view diagram of a length of tubing constructed by joining two shorter tubes.
Figure 3C:
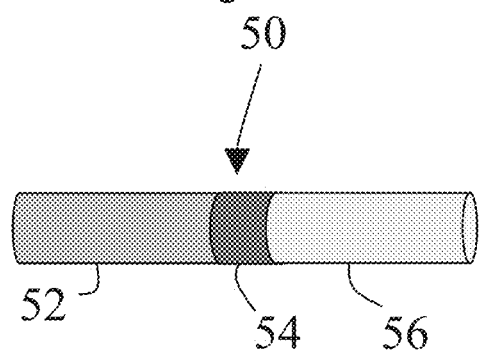

FIG. 3a and FIG. 3b show one of many examples of construction and methods to construct the framework 12 of the present invention from constitutive components. FIG. 3a is a perspective view of a section of composite framework member 40, and FIG. 3b is an elevational cross sectional view of the same section of composite framework member 40. FIGS. 3a and 3b provide a non-limiting example of construction of the present invention's algae cultivation system wherein there are ballast tubes 42 for the culture, ballast tubes 44 for the surrounding water, and/or pipes 46 for process fluids like nutrient feeds. Spacers 48 are included to protect the tubes from damaging each other, and a variety of circumferential bands 26 and points of attachment 36 are shown. FIG. 3c is a perspective view of a section of tube 50 showing an example of the present invention where the cultivation system is constructed from smaller tubes 52 and 56 joined by coupler 54. Furthermore, bundling sections of composite framework members 40 together and coupling them with other bundles enables construction of frameworks of almost unlimited size.

Figure 4A:
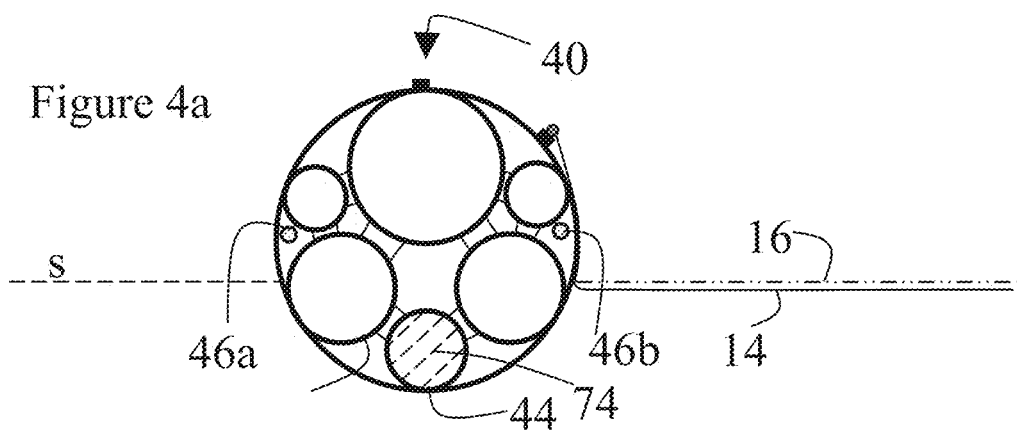
FIGS. 4a-4d are elevational cross sectional view diagrams of a portion of a cultivation system of the present invention at different stages of the submersion and surfacing processes.

FIGS. 4a-4d are drawings of elevational cross sectional views of a portion of a floating pond. FIG. 4a depicts the pond during normal growing operations. The composite framework section 40 sits high on the surface s. The bottom most ballast tube 44 for surrounding water 74 is filled to stabilize the composite framework member 40. All ballast tubes 42 for the culture are empty. The culture 16 is exposed to sunlight, wind, and waves. It is separated from the surrounding water by the framework 40 and liner 14. Nutrients are introduced from a supply pipe 46a, and culture is harvested through pipe 46b. The mooring system and submerging lines are not shown. Supply pipe 46a and harvest pipe 46b can connect between the culture and either to ships, platforms, buoys, floating tanks, a piping network, or a combination thereof.

Figure 4B:
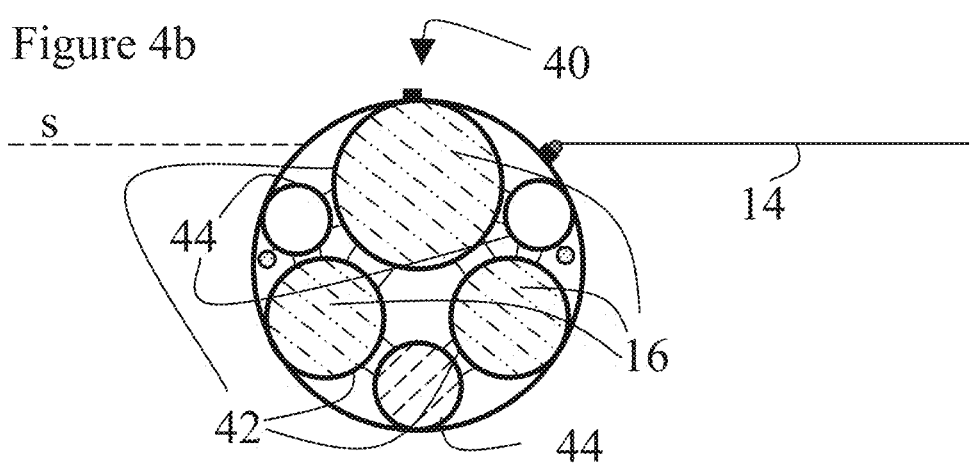

FIG. 4b is a drawing of the floating pond after at least a portion of the culture 16 has been used to fill the ballast tubes 42. In this embodiment, the liner 14 is made of materials less dense than the surrounding water and floats. Substantially all of the culture 16 has either been harvested or used to fill the ballast tubes 42. The composite framework 40 sits much lower in the surrounding water. Two of the three ballast tubes 44 for the surrounding water are still empty. The ballast tank of this invention can be of any suitable shape and material. Such materials for construction of the ballast tank can include, but are not limited to, metal, fiberglass, plastic and the like.

Figure 4C:
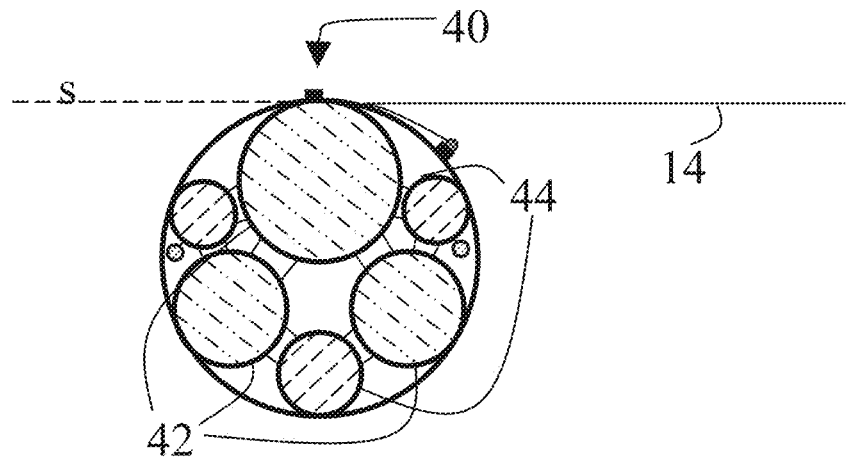

FIG. 4c is a drawing of the floating pond after the remaining two ballast tubes 44 for surrounding water are full. This shows the composite framework section completely or nearly completely submerged. Referring to FIG. 2, submerging lines 32 are spooled to increase their weight and submerse the floating pond. The orientation and depth of the floating pond is controlled by the amount of submerging lines 32 on their winches 34.

Figure 4D:
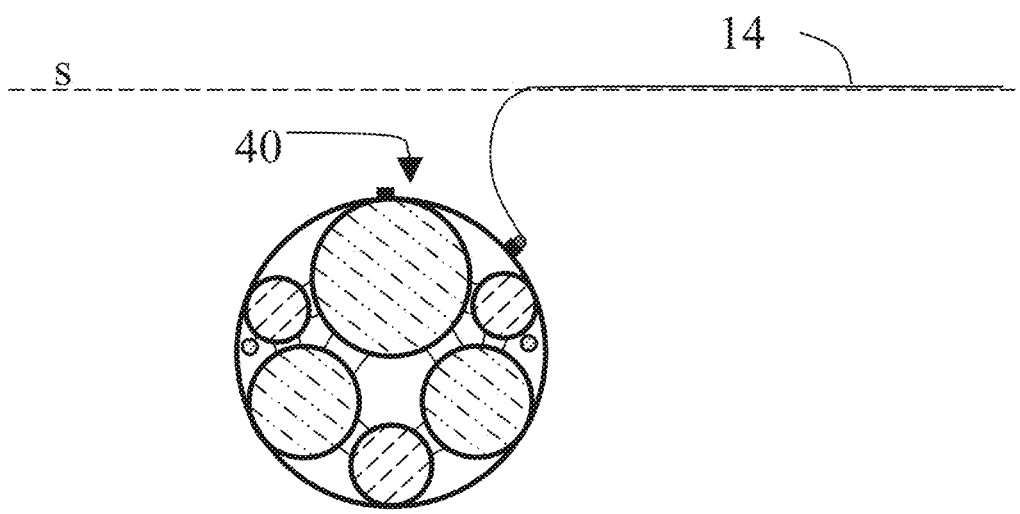

FIG. 4d is a drawing of the floating pond on its way to the surface s. Referring to FIG. 2 again, submerging lines 32 are unspooled until the composite framework section 40 is just below the surface s of the surrounding water. In one embodiment of the present invention, in which the liner is less dense than the surrounding water, the liner floats, trapping very little water and, thus, eliminating the need to pump large volumes of water out of the floating pond before refilling it. The top two ballast tubes 44 for the surrounding water are filled with air, and the floating pond becomes configured and positioned as shown in FIG. 4b. Once the culture is emptied from the ballast tubes 42 to fill the pond and additional water and nutrients are added as needed, the floating pond is again ready for growth of the culture as depicted in FIG. 4a.

Figure 5A:
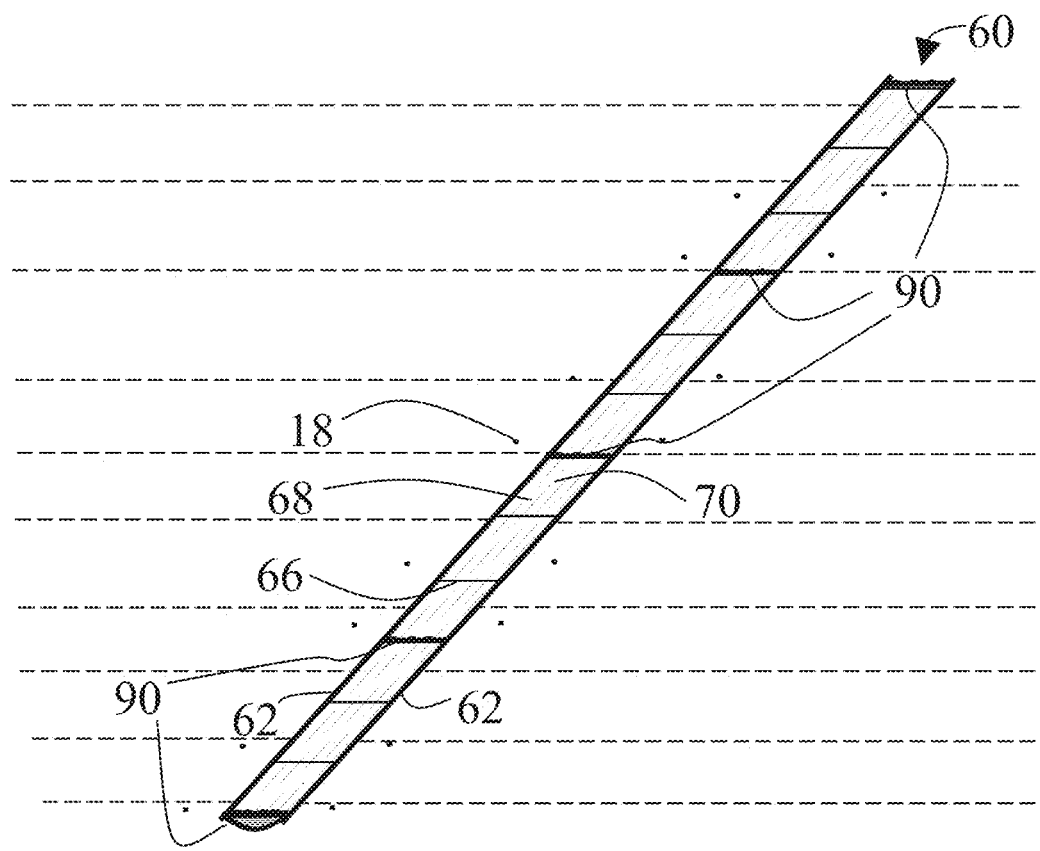
FIG. 5a is a perspective view diagram of a rectangular floating pond of the present invention.
Figure 5B:
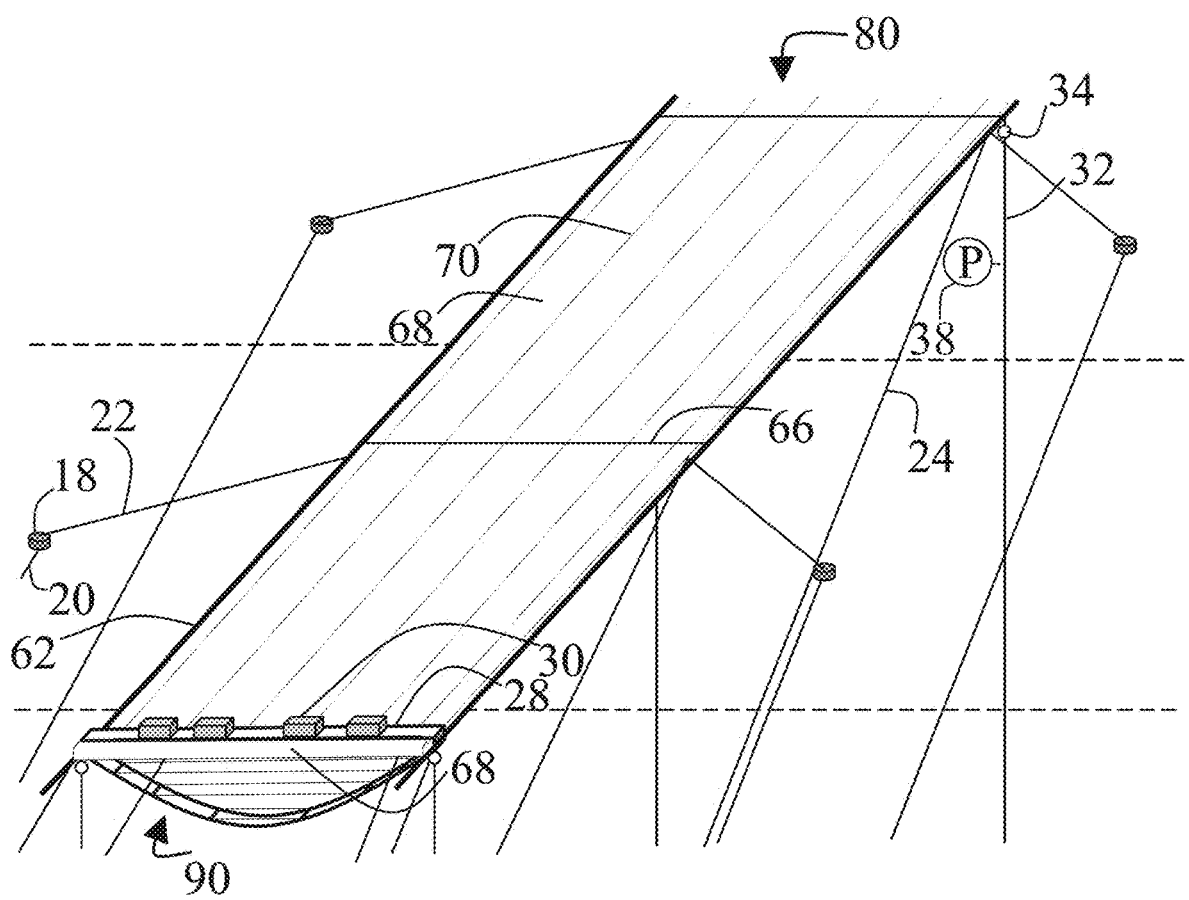
Figure 5C:
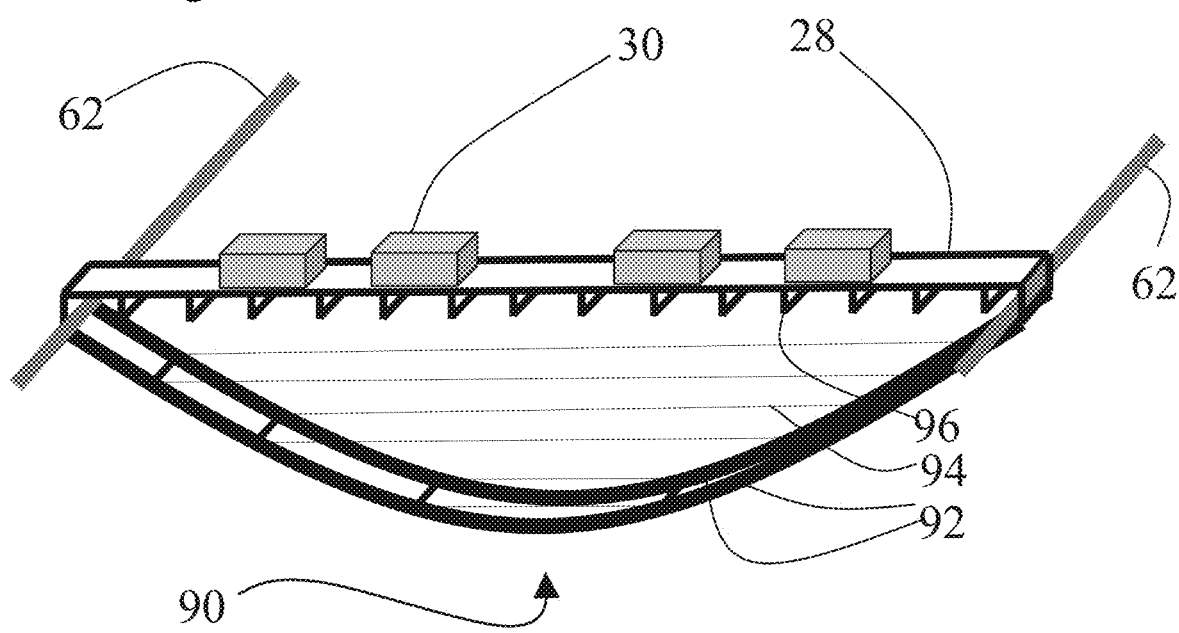

FIG. 5a is a drawing of a rectangular floating pond 60 of the present invention, a design appropriate for large ponds hundreds of meters wide and several kilometers long or larger. Mooring buoys 18 and transverse supports 66, which may be anything known to one of ordinary skill in the art, including, as non-limiting examples, rods or cables, stabilize the position and integrity of the structure, respectively. The liner 68 is attached to longitudinal members 62, and the culture 70 is contained within the liner 68 and the buoyant framework consisting of the longitudinal members 62 and transverse members 90. FIG. 5b is a more detailed perspective view of a section 80 of the rectangular floating pond 60 depicted in FIG. 5a. The additionally labeled components are mooring lines 20 connecting the mooring buoys 18 to the subsurface, mooring lines 22 connecting the buoyant framework to mooring buoys 18, mooring lines 24 connecting the buoyant framework to the subsurface, a platform 28, equipment 30, submerging lines 32, and winches 34. In this embodiment, the liner 68 is folded up and attached to the transverse member 90. Further details of the longitudinal 62 and transverse 90 members are shown in the perspective view of FIG. 5c, where only illustrative components from a section of floating pond 60 are drawn, including a platform 28 and equipment 30. Shown are components of the transverse member 90, including arced members 92, supports 94 such as rods or cables, and platform supports 96 that float on top of the culture (not shown), liner (not shown), and surrounding water (not shown). In this and other embodiments of the present invention, the desire to place the transverse member 90 either at the end or middle of long ponds necessitates its construction so that it surrounds the longitudinal members 62 and does not penetrate them nor the liner (not shown) attached between them.

Figure 6A:
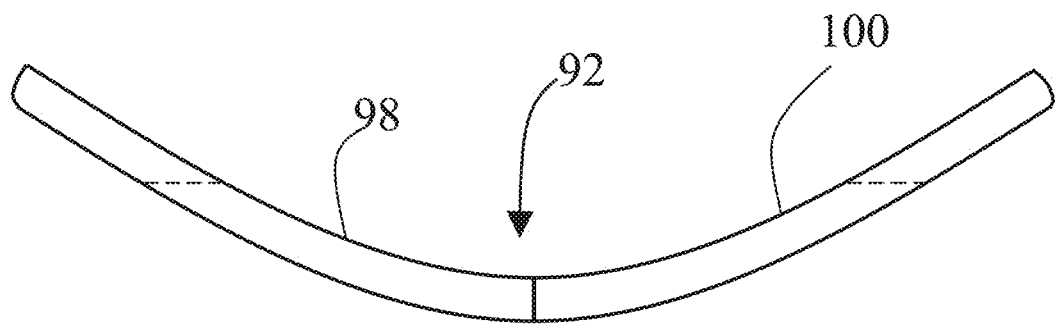
FIGS. 6a and 6b are elevational cross sectional view diagrams of an arced member 92 that is a component of the transverse member 90 from the diagram in FIG. 5c.
Figure 6B:
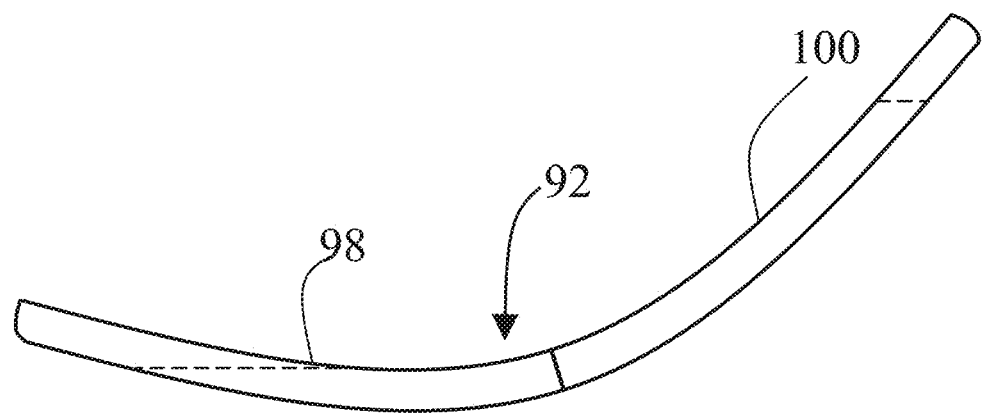

FIG. 6a and FIG. 6b are drawings of elevational cross section views of an arced member 92 that is a component of transverse member 90. The embodiment shown in this Figure is one wherein it is desirable to keep the floating pond level during submersion. As shown, it can support the weight of equipment positioned on the transverse member 90 and be used as a ballast tank to help keep the floating pond 60 balanced during surface operation. The arced member is split into two equal halves, LHA member 98 and RHA member 100. If the pond tilts as shown in FIG. 6b while submerged, the forces and torques on the arced member 92 bring it back to the position shown in FIG. 6a.

Figure 7A:
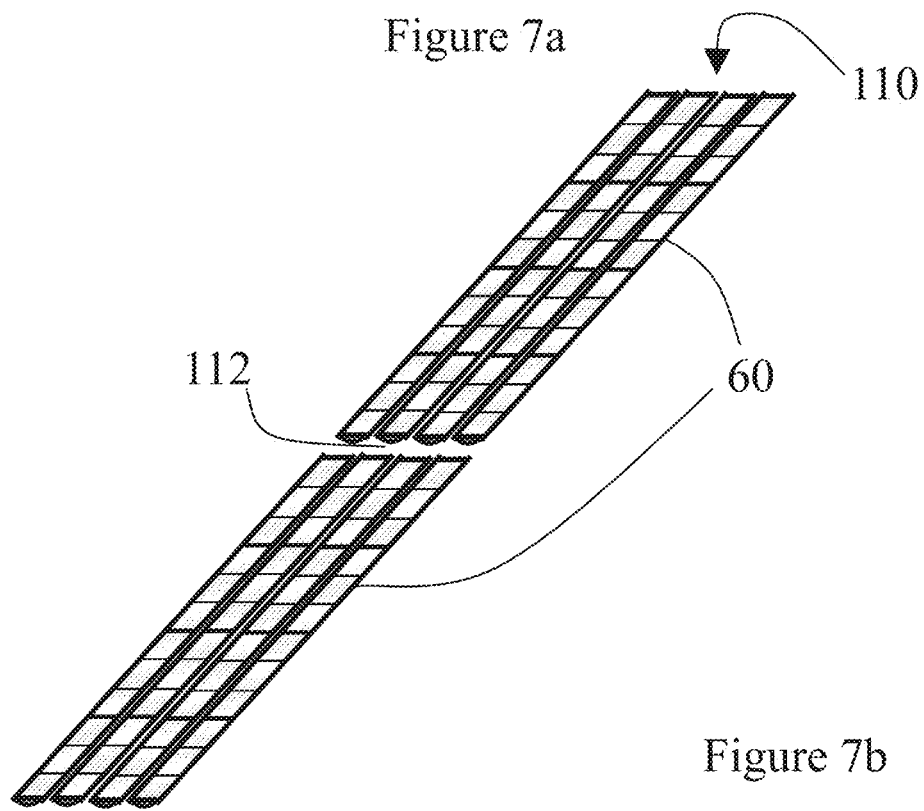
FIGS. 7a and 7b are perspective view diagrams of farms consisting of cultivation systems of the present invention.
Figure 7B:
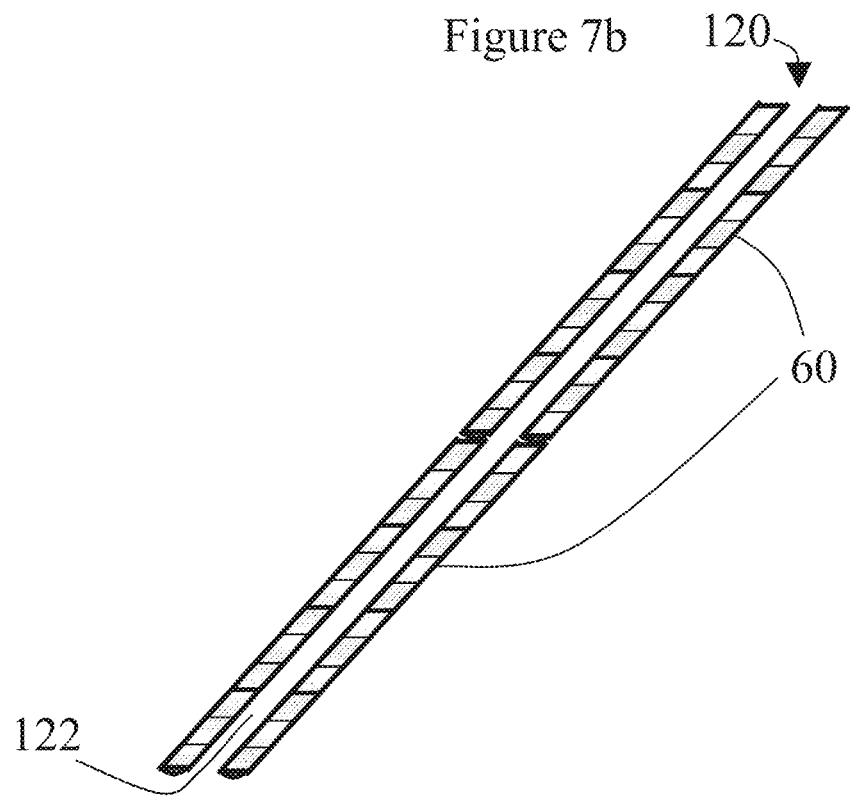

FIG. 7a and FIG. 7b are drawings of two embodiments of many possible arrangements of rectangular floating ponds into farms. In each, the floating ponds 60 are arranged in rows and can be connected to each other with piping. In FIG. 7a, the rows contain floating ponds 60 positioned very closely together with an open water channel 112 separating the rows. An advantage of this arrangement is dense packing of the floating ponds in farm 110. In FIG. 7b, the rows contain floating ponds 60 positioned with more space between each one, forming an open water channel 122 between adjacent ponds. In this regard, the present invention includes an embodiment for an accessible arrangement of floating ponds where, for example, each floating pond 60 in farm 120 is equally accessible, although less of the total area of farm 120 is occupied by floating ponds 60 than in farm 110. Of course, each farm can extend over much greater areas than shown in FIG. 7 and contain many more floating ponds.

Alternate embodiments of the present invention use other methods for joining the cultivation systems together. For example, as in U.S. Pat. No. 6,854,408 to De Baan, an apparatus is disclosed for mooring to floating vessels side-by-side, and this method can be used with the present invention. In this embodiment, the first floating pond is moored to the seabed by a single point mooring system. The apparatus comprises an arm with proximal and distal ends and the arm is mountable on the first floating pond for rotation about a vertical axis and the distal end projects outwardly from the first floating pond in use. A substantially inelastic mooring line is attached to the distal end of the arm and is securable to the second floating pond. The resilient means is operable to allow limited rotation of the arm about the axis in the first direction in response to tension in the mooring line which exceeds a pre-determined value. The resilient means automatically restores the arm to its former position upon reduction of the tension below the predetermined value. The arm is freely rotatable about the axis in a second direction opposite to the first direction. The resilient means can comprise a piston and cylinder mountable to the first floating pond adjacent the arm such that rotation of the arm in the first direction brings the arm into contact with the piston and to compress the piston into cylinder when the tension on the mooring line exceeds the predetermined value, and wherein the cylinder is operable to extend the piston upon reduction of the tension below the predetermined value. Alternatively, the resilient means may comprise a stop member mountable on the first floating pond such that rotation of the arm in the first direction brings the arm into contact with the stop member, and a piston and cylinder mounted on the distal end of the arm between the arm and the mooring line and operable to extend when the tension on the mooring line exceeds the predetermined value, and to retract upon reduction of the tension below the predetermined value. In another embodiment, these methods may be used with the rectangular floating pond 60.

Figure 8:
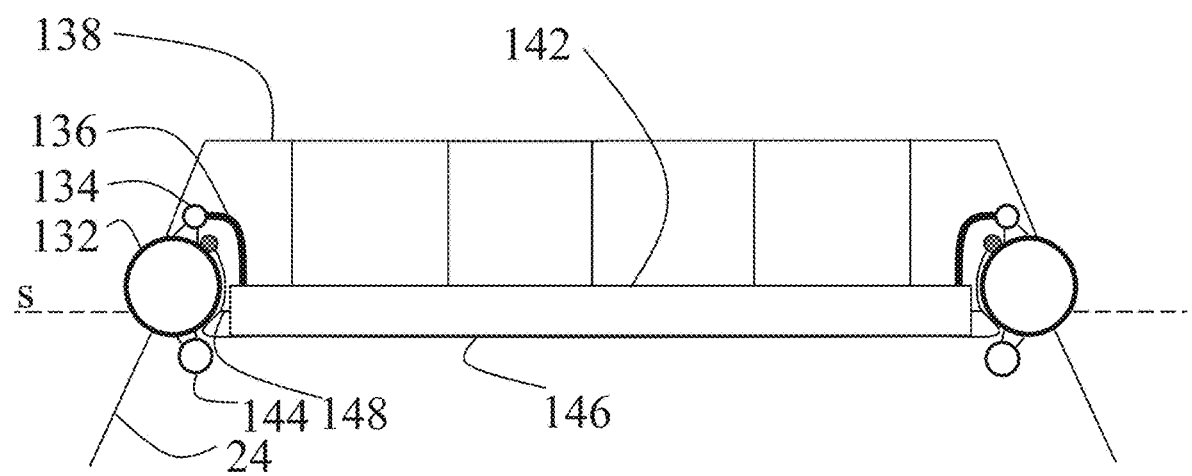
FIG. 8 is an elevational cross sectional view diagram of an alternative embodiment of a cultivation system of the present invention.

FIG. 8 is an elevational cross sectional view of a small rectangular floating pond. The buoyant framework consists of two longitudinal members, with crossbar supports 138 spanning between them. The longitudinal members are composites, consisting of a buoyant 24 inch (approximately 60 cm) diameter longitudinal tube 132 and a 6 inch (approximately 15 cm) diameter longitudinal tube 134 to manage the culture. Optionally, short sections of tubing 144 are placed at the ends of the ponds to compensate for any extra weight added to the framework by pumps or pipes. Pipes, axially slit 12 inch diameter pipes 142 attached to crossbar supports 138, are included as inlets and outlets to add and remove the culture and/or makeup water to and from the pond. Circumferential bands provide points of attachment between the tubes. The liner 146 is attached to longitudinal tube 132 and folded up (not shown) and attached to a crossbar support spanning between the longitudinal members. The culture 148 grows in the pond, and the current is maintained by recycling the culture from the downstream end of the pond to the upstream with suitable pumps (at least two) and pipes 136 connecting longitudinal tubes 134 to slit pipes 142 to fill the pond on the upstream side and empty it on the downstream side. The pond is kept from drifting by mooring lines 24 anchored to the subsurface. Alternatively, the pond can be attached to a mooring buoy, or other suitably anchored point, as shown in FIG. 1.

Figure 9:
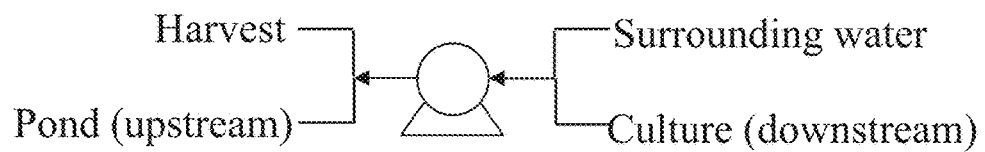
FIG. 9 is a schematic diagram of pump connections for use with the cultivation system of the present invention depicted in the diagram in FIG. 8.

FIG. 9 is a schematic showing pump lines used in conjunction with the floating pond in FIG. 8 to alternate between uptaking surrounding water, downstream culture, or a mixture at their inlet (downstream slit pipe 142) and delivering them to harvest tanks, the upstream slit pipe 142, or a mixture at their outlet.

DETAILED DESCRIPTION OF THE INVENTION

Definitions

The term algae, as used herein, is meant in its broadest sense to include any organism with chlorophyll a and lacking a differentiated thallus. As such, the definition includes both eukaryotic and prokaryotic organisms.

As used herein "algae" refers to any of various chiefly aquatic, eukaryotic, photosynthetic organisms, ranging in size from single-celled forms to the giant kelp. The term may further refer to photosynthetic protists responsible for much of the photosynthesis on Earth. As a group, the algae are polyphyletic. Accordingly, the term may refer to any protists considered to be algae from the following groups, alveolates, chloraraachniophytes, cryptomonads, euglenids, glaucophytes, haptophytes, red algae such as Rhodophyta, stramenopiles, and viridaeplantae. The term refers to the green, yellow-green, brown, and red algae in the eukaryotes. The term may also refer to the cyanobacteria in the prokaryotes. The term also refers to green algae, blue algae, and red algae.

As used herein, a mooring line is a submersion line, a chain, a rope, strap, pipe, cord or any other type of line used to tie a floating object to a docking object.

In certain embodiments, the methods, apparatus and systems disclosed and claimed herein provide for algae cultivation. In certain embodiments, the methods, apparatus and systems disclosed and claimed herein provide for biofuel production from algal culture. In one embodiment, the algae cultivation systems disclosed herein are operated in an outdoor environment. One embodiment concerns methods and an apparatus and systems for producing biodiesel. High oil strains of algae are cultured in the algae cultivation system of the present invention and harvested. In one embodiment, oil is separated from the algal cells and processed into diesel using standard transesterification technologies such as the well-known Connemann process (see, e.g., U.S. Pat. No. 5,354,878, the entire text of which is incorporated herein by reference). In one embodiment, oil is produced and separated by chemical liquefaction (Dote, 1996; Matsui, 1997). In one embodiment, methane rich gas is produced by low temperature gasification (Minowa, 1999). However, it is contemplated that any known methods for converting algae into biodiesel may be used.

In some embodiments, the algae cultivation system may be used directly to provide an animal or human food source, for example by culturing edible algae such as *Spirulina*. In other embodiments, the algae cultivation system may be used to support growth of a secondary food source, such as shrimp or other aquatic species that feed on algae. Methods of shrimp farming and aquaculture of other edible species are known in the art and may utilize well-characterized species such as *Penaeus japonicus, Penaeus duorarum, Penaeus aztecus, Penaeus setiferus, Penaeus occidentalis, Penaeus vannamei* or other peneid species. The ordinarily skilled artisan will realize that this disclosure is not limiting, and other edible species that feed on algae may be grown and harvested. In other embodiments, the system, apparatus and methods are of use for removing carbon dioxide pollution, for example from the exhaust gases generated by power plants, factories and/or other generators of carbon dioxide.

In an embodiment of the present invention, the depth of the algae cultivation system, the pond or apparatus of the current invention, is maintained between 0 cm and 50 cm. In one embodiment of the present invention, the depth is maintained between 0 cm and 10 cm. In another embodiment of the present invention, the depth is maintained between 10 cm and 30 cm. In another embodiment of the present invention, the depth is maintained more than 50 cm. The depth, combined with the amount of algae cultivated therein, can be selected to optionally shade algae near the bottom of the pond, trough, or apparatus by a dense upper algae population near the top of the water volume. In this manner, another embodiment of the present invention provides for a two stage growth by selecting conditions to create such a bi-layer of algae, i.e. dark lower volume and a light upper volume, which acts to at least partially block light from the lower volume.

The framework 12 of the present invention is designed to provide adequate support to the liner 14 so that the culture 16 is largely separated from the surrounding water. Some exchange of the culture 16 and surrounding water is permissible, as long as gross dilution or loss of the culture is prevented.

In its simplest form, the floating pond of the present invention, e.g. floating pond 10 from FIG. 1 or 60 from FIG. 5*a*, can be placed in a sheltered environment, such as a bay, where it will not be exposed to weather extremes. This enables the floating pond subcomponents to be designed to withstand only moderate stresses compared to those generated during violent weather in the open ocean. However, this presents two distinct disadvantages. First, it limits the number of sites where the pond can be installed. Second, the sheltering limits the mixing forces that the wind and waves supply to the pond.

Alternatively, the floating pond can be constructed and operated during mild conditions and disassembled and stored safely during violent weather. This increases the number of potential sites for the pond, as opposed to protected, sheltered sites, and it also increases the exposure of the floating pond to waves and winds. In one method of the present invention, the floating pond is designed and constructed/installed in such a way as to utilize the wind in the cultivation system. The floating pond now can be installed in any open water location and can take advantage of unsheltered mixing from the wind and waves. However, their will be operating costs associated with the repeated assemblies and disassemblies of the pond, and growth time will be lost during these operations. This might be acceptable for test ponds but is suboptimal for production ponds.

Embodiments of the present invention provide a floating pond with a mooring line. Another embodiment of the present invention provides a circular floating pond 10 with a mooring line. An additional embodiment of the present invention provides a rectangular floating pond 60 that is moored or has a mooring line. Those of ordinary skill in the art will understand the many possible options for mooring and/or tethering the floating pond. As a non-limiting example of this information, there are many articles by Dr. Mark Grosenbaugh, including Grosenbaugh, M. A. 1996. On the dynamics of oceanographic surface moorings. Ocean Engineering 23, (1) (JAN): 7-25; and Grosenbaugh, M. A. 1995. Designing oceanographic surface moorings to withstand fatigue. Journal of Atmospheric and Oceanic Technology 12, (5) (OCT): 1101-10. These describe possible mooring systems which may be used with the present invention. In one aspect, the floating pond of the present invention further comprises a mooring system. In an additional aspect of the present invention, the mooring system is constructed from one or more of a cable, a chain, a rope, or a tether assembly, which will be suitable to anchor the floating pond. Another aspect of the present invention provides a floating pond with a mooring system suitable to anchor the floating pond in its intended environment (for example, there will be some instances of the present invention in which suitable mooring systems for a lake will not be all the same as suitable mooring systems for the ocean). In another embodiment of the present invention, the mooring system will fix the floating pond to a desired location or orientation in relation to other floating ponds. In an additional embodiment of the present invention, the mooring system consists of more than one mooring line. Another embodiment of the present invention provides a floating pond with a mooring system that has sufficient slack in the line so as to allow some mobility for the floating pond, and in particular sufficient mobility to maximize transfer of $CO_2$ in the algae cultures being cultivated. In still other embodiments of the present invention, the mooring system may be constructed from elastic or somewhat elastic materials to allow for flexibility, such as rubber tethers, synthetic rope, or other materials known to one of ordinary skill in the art. Other embodiments of the present invention include a mooring system constructed from a chain or from a pipe. Algorithms provided by Grosenbaugh, et al. and known to those ordinarily skilled in the art may be applied to the present invention in order to provide specific mooring systems for the present invention, adapted to the intended environment in which the floating pond will be installed.

The mooring line, mooring system, or buoy system used in the present invention may be any known to those of ordinary skill in the art. In one embodiment, the floating pond of the present invention will have a buoy and an anchor comprising: a section of cable connected to a buoy. This may additionally comprise an energy absorbing cable, may additionally comprise a weighted cable, and may additionally comprise a buoyant cable connected to the anchor, as disclosed in Nye, et. al., U.S. Pat. No. 7,244,155 and facilitating, through a smooth transitional series of connections. comprising a protected cable and being connectable to said buoy; a second section comprising an energy absorbing cable; a third section comprising a weighted cable; and a fourth section comprising a buoyant cable and being connectable to said anchor; where said sections being connected in series by a smooth transitional connection; and when said mooring line being deployed, said mooring line securing said buoy to said anchor and having an inverse catenary lay. Smooth transitional connections may be included in mooring line. Smooth transitional connections may be for connecting the mooring line with the weighted cable, with the energy absorbing cable, with the buoyant cable with the anchor in series so that the sections are smooth from one section to the next. Smooth transitional connections may be any connection capable of connecting the four sections in series so that the sections are smooth from one section to the next. For example, smooth transitional connections may be smooth transitional machine splices, or braider splices, as commonly know in the art. Smooth transitional connections may allow for mooring line to be rolled up on a continuous reel or box that prevents mooring line from having to be shackled together as it is payed out of a vessel. Inverse catenary lay may be the shape mooring line takes when mooring line may be deployed. Inverse catenary lay may be for allowing mooring line to store length for the various depths of the ocean. Inverse catenary lay may be for preventing mooring line from sinking to the bottom and fouling up from rubbing on anchor or the ocean bottom.

In one or more embodiments, a floating pond, or the floating pond 10, or the floating pond 60 can include one or more mooring lines, such as three or more, and the mooring lines can be used to fix the position of a floating pond. In one or more embodiments, the mooring line(s) are attached to the lower portion of the floating pond. In one or more embodiments, the mooring line can include two or more miles of between 4 and 6-inch diameter line of rope, cord, polymer-coated rope, chain, wire or any combination of these. In one or more embodiments, the length of the mooring line can be about equal to the water depth. In alternate embodiments, the length of the mooring line can be about equal to 2 to 3 times the water depth. The mooring line can be anchored to the ocean or sea floor. In one or more embodiments, the mooring line consists of protected cable made of liquid crystal polymer. In one or more embodiments, the mooring line consists of protected cable comprising a polyester cable. In another embodiment, the polyester cable is up to seven hundred (700) meters of twelve (12) strand polyester with a rated breaking strength of seventy five hundred (7500) pounds. In another embodiment, the polyester cable is up to seven hundred (700) meters of twelve (12) strand polyester with a rated breaking strength of thirty-four hundred (3400) pounds. In an additional embodiment, the polyester cable is more than seven hundred (700) meters of twelve (12) strand polyester with a rated breaking strength of seventy five hundred (7500) pounds. In an additional embodiment, the polyester cable is more than seven hundred (700) meters of twelve (12) strand polyester with a rated breaking strength of more than seventy five hundred (7500) pounds. The mooring line may additionally include any known means to one of ordinary skill in the art to afford the mooring line fish bite protection. The mooring line may include any known means to one of ordinary skill in the art to afford the mooring line strum protection, which may include, as a non-limiting example, a polyurethane jacket over the protected cable with external ridges. In another embodiment, the present invention includes a mooring line that is non-conductive. In another embodiment, the present invention provides a mooring line comprising a conductor.

An additional embodiment of the present invention avoids the additional costs incurred by assembling and disassembling the cultivation system and/or floating pond by providing a floating pond (e.g. floating pond 10 and/or floating pond 60) that is submersible. In one embodiment of the invention, a floating pond is constructed so that it is submersible. As such, the floating pond subcomponents are designed to withstand moderate stresses compared to those generated during worst case weather in the open ocean, but now without needing to place the pond in a sheltered environment or the need to disassemble it during harsh conditions. In FIG. 1 the submerging lines 32 are free hanging lines connecting the floating pond 10 to the subsurface. In one embodiment of the present invention, the submerging lines 32 are connected to winches 34 that vary the amount of submerging line 32 on the winch 34 and, therefore, off the subsurface.

Additional embodiments of the present invention provide for methods of modulating the buoyancy of the framework of a floating pond or apparatus of the present invention. In one embodiment, the framework of a floating algae cultivation system is filled or partially filled with algae culture, thereby lessening the buoyancy. In another embodiment, this is done to further submerse the floating pond and provide some protection from potentially damaging climate or storm conditions. In another embodiment of the present invention, the framework of a floating algae cultivation system is filled or partially filled with surrounding water, thereby lessening the buoyancy. In another embodiment of the present invention, the buoyancy of a floating algae cultivation system is modulated through the use of submerging lines and spool adjustments. As a non-limiting example, when the floating pond descends, the submerging lines 32 coil on the subsurface subs, decreasing their net weight until an equilibrium is established at a given depth for the floating pond, as shown in FIG. 2b. The arrangement of the submerging lines 32 is such that they can be used to set the depth and orientation of the floating pond 10. Depth gauges and level gauges can be used to guide this. Use of the submerging lines 32 and winches 34 establishes a stable submersion system. Valves and systems to fill and empty the framework with liquids and air are well known to those ordinarily skilled in the art and may be used to modulate buoyancy on the system disclosed herein.

In one or more embodiments of the present invention, one or more tubes used in the construction of the submersible floating pond are equipped with pressure sensors. Said pressure sensors are used to adjust the components of the submersible floating pond to control the submersion depth of the pond to one commensurate with a set pressure. In another embodiment of the present invention, one or more tubes used in the construction of the submersible floating pond is equipped with pressure relief valves to limit the differential pressure between the surrounding water and the interior of the tubes. Said differential pressure is set within the safe specification of said tubes.

In one embodiment, the invention presented herein may be of inseparable construction. Other embodiments, however, employ a modular approach for reasons of manufacturability, maintenance, upgradeability, and expandability, in its various respects. Thus the system is applicable to a broad variety of modes and means of cultivation, and the presentation thereof to a submarine current.

In one embodiment of the current invention, the floating pond is suspended (that is, between ocean floor and surface) horizontally during submersion. In alternate embodiments, the floating pond may be suspended in an attitude ranging from horizontal to vertical. The floating pond is restrained by mooring lines that are themselves anchored to the seabed, with the floating pond itself remaining positively buoyant enough to keep such lines taut and its position thus fixed. In an alternate embodiment, the floating pond may be restrained by mooring lines still, however in a manner so as to allow more mobility of the floating pond in response to water motions. The floating pond of the present invention may have a single mooring line. The floating pond of the present invention may have more than one mooring line. The floating pond of the present invention may have 2, 3, 4, 5, 6, 7, 8, 9, or 10 or more mooring lines. An additional embodiment of the present invention provides that the free end of each mooring line assembly is retained at the surface by specialized buoys, while the anchored end may be at a great depth. Between anchor point and maximum-depth operational position, the mooring lines are preferably affixed with flotation devices, allowing the burden borne by the buoys to be only that of the length of mooring line between the surface and said maximum operational depth. The anchoring technologies relied upon herein are essentially those typically employed for offshore oil platforms. As mentioned above, in another embodiment of the present invention part or all of the modulation of the floating pond's submersion, ascension and descent, is due to the submersion line(s) and/or mooring line(s) coiling on the sea floor, removing weight from the pond, and the weight of the mooring line affecting the descent. Another embodiment provides that in addition to the mooring line modulating the floating pond's buoyancy are ballast tubes 42.

In one embodiment, the floating pond may have, for a controlled means of descent and ascent, an on-board winch system. In concert with buoyancy control of the floating pond, through methods known to one of ordinary skill in the art or as disclosed in the present application, the winch system enables the floating pond to "crawl" down its mooring lines from the surface, and to likewise ascend (assisted by variable buoyancy) for harvesting, maintenance or other purposes. The winches may be of a "take-up" design (e.g., a drum reeling a cable thereon); other embodiments, however, employ (in the region of operational descent) chains that are readily engaged for tractive purposes, thereby obviating the need for take-up drums or other on-board holding facilities, and precluding any added mass onboard the platform assembly.

In regards to deployment, the fully buoyant floating pond in one embodiment is first towed at surface into position (i.e., amongst or near the mooring line buoys). Alternatively, the floating pond may be self-powered for surface transit, though such is not the case in the preferred embodiment (wherein sensitive mechanisms are intended to be kept to a minimum). With the platform still at the surface, the mooring lines are retrieved and threaded into or onto the winch assemblies. Once all is secured, and upon remote command, certain ballast tanks are (in controlled fashion) flooded so as to produce the appropriately reduced displacement, as the winch assemblies begin pulling the platform down to its preferred operating depth. Ascension is essentially the reverse of this operation.

In one embodiment of the present invention, the presence of substantially unidirectional ocean current is taken advantage of to maintain adequate separation between mooring lines and keeping all lines from entanglement. Said current further serves to fix the floating pond in operating position by virtue of its forces being reacted by the platform's mooring lines.

Additional embodiments of the present invention include the use of retractable lines to facilitate the positioning of the floating pond while on the surface, during submersion, and/or during surfacing. Use of a retractable line enables rapid re-establishment of a prior configuration following a shift away from said configuration.

In one embodiment of the present invention, equipment to control the position and operation of the floating pond are located on said floating pond. In one embodiment of the present invention, equipment to control the position and operation of the floating pond are located remote to said floating pond, such as on a buoy, a different floating pond, a boat, a satellite, or on land. In another embodiment of the present invention, some equipment to control the position and operation of the floating pond are located on said floating pond and some equipment are located remote to it as described above. Methods of transmitting signals between a remote location and the floating pond are well known to those of ordinary skill in the art.

One embodiment of the present invention includes a method of construction of the cultivation system as shown in FIGS. 3a and 3b. Although there is a practical limit to the diameter of plastic tubes, the use of a collection of tubes enables construction of larger floating ponds and larger cultivation systems than would otherwise be possible. An additional embodiment of the present invention is a cultivation system with more than one tube and said two or more tubes are used for two or more collection purposes. In one embodiment, the present invention provides an algae cultivation system comprising a floating pond with one or more ballast tubes. In another embodiment, the present invention provides a floating pond with one or more ballast tubes filled with one or more of water, air, algae culture, surrounding water, or nutrients. In another embodiment, the invention further consists of spacers 48. In an additional embodiment, floating ponds of the present invention are bundled to have 2, 2 or more, 3, 3 or more, 4, 5, 6, 7, 8, 9, 10, 11, 12, 13, 14, 15, 16, 17, 18, 19, 20-25, 26-30, 31-40, 41-50, 51, or 52 or more tubes bundled together.

In one embodiment of the present invention, the algae culture 16 is exposed to sunlight, wind, and/or waves when ballast tubes 42 are emptied of culture or are full of air. In another embodiment, the liner 14 is made of materials less dense than the surrounding water and, thus, floats. One embodiment of the present invention provides for the use of materials less dense than the surrounding water, for example components including the framework 40, the tubes, the spacers, additional tubes, or tubes and spacers, to make them buoyant. Another embodiment of the present invention provides components including the framework 40, the tubes, the spacers, additional tubes, or tubes and spacers made buoyant with air to modulate the framework's buoyancy. An additional embodiment of the present invention provides the modulation of buoyancy of the framework of a floating cultivation pond and/or the tubes by using the algae as ballast (e.g. as shown in FIG. 4 where algae culture fills ballast tubes 42).

In another embodiment of the present invention, submerging lines 32 and winches 34 are used to modulate the floating pond's buoyancy. In one embodiment, submerging lines and winches are used in combination with ballast tubes.

There are many advantages to the cultivation system described in FIGS. 1-4 as described in the Summary of the Invention. Use of an aquatic floating pond avoids the pond from competing with other uses for land. Furthermore, it avoids costs associated with terrestrial locations like site leveling. Exposure of components to floating or submerged conditions limits the weight and stresses to which they are exposed, thereby enabling use of materials and geometries unsuitable for terrestrial installation. Use of tubes and piping for the framework of the floating pond simplifies construction and scaling to large ponds. A circular geometry for the floating pond is depicted in FIGS. 1-4. However, the circular geometry depicted doesn't tie in well with unidirectional winds and currents, nor does it allow for efficient arrangements of combinations of floating ponds to form large farms.

Alternate embodiments of the present invention provide rectangular floating ponds, which can more fully utilize and thrive from some environmental conditions, such as when the floating pond is somewhere with unidirectional winds and currents. Another embodiment includes rectangular floating ponds arranged in combination, two or more, in a space-efficient manner—linear, rectangular, square—and in some instances, in a farm. In one embodiment of the present invention, rectangular floating ponds are arranged in combination, line, or block. Rectangular floating ponds of the present invention may be combined so as to inhibit twisting, turning, or shifting, and in this manner are well suited to algae cultivation with unidirectional winds and currents As a non-limiting example this could be on the ocean. Rectangular floating ponds may be used to make efficient use of space and/or the available sunlit area. Rectangular floating ponds of the present invention may be used in an additional embodiment to create a more efficient system for cultivation and collection. FIG. 5a is a perspective view of one possible rectangular floating pond 60. The buoyant framework consists of both longitudinal members 62 and transverse members 90. Both members can be composite framework members involving many subcomponents. In embodiments of the invention, the longitudinal members 62 are aligned parallel to the wind. This allows for maximal mixing of the floating pond 60 and a current of the culture 70 to establish itself moving parallel to the longitudinal members 62. The longitudinal members 62 are depicted extending in both directions past the liner 68 and transverse members 90 to facilitate connecting its constituent pipes to other ponds, ships, platforms, piping networks, etc. The plurality of transverse members 90 enables for the efficient management of culture along the entire length of the pond and between two consecutive transverse members 90. Judicious harvesting and replenishment of nutrients at each transverse member allows for efficient operation. The present invention also provides for smaller rectangular floating ponds with a simpler framework design, including ones without transverse members, whereby the liner is folded up at both ends of the longitudinal members to isolate the pond from the surrounding water. The present invention also includes smaller rectangular floating ponds with transverse members. In one aspect of the present invention, the rectangular floating pond can have a width of about 1 m to about 3 m. In one aspect of the present invention, the rectangular floating pond can have a width from about 3 m to about 20 m. In one aspect of the present invention, the rectangular floating pond can have a width from about 20 m to about 70 m. In one aspect of the present invention, the rectangular floating pond can have a width from 70 m to about 200 m. In one aspect of the present invention, the rectangular floating pond can have a width greater than 200 m, although other widths can also be suitable.

Another advantage of the embodiment of the current invention as rectangular floating ponds is that they can be efficiently arranged into farms. One particular embodiment of the present invention, wherein the cultivated algae are used to produce oil, is to provide a meaningful amount of oil and utilize large scale production.

In certain embodiments, the algae cultivated to produce biofuel are not genetically engineered. Natural strains of algae, or even strains occurring naturally in the immediate vicinity of the pond, are cultivated without genetic alteration. In certain embodiments, large amounts of biomass are generated without regard to the constitutive species. In certain embodiments, large amounts of biomass are generated using conditions that cause the preferential growth of one algal species over others. For example, extremes of pH or salinity can be used to enrich for *Spirulina* or *Dunaliella* (Richmond, 1986).

In one embodiment, the floating pond produces algae, the specifications of said algae varying dependent upon the type of algae and the intended use. For example, some species which may be cultivated in the floating ponds of the present invention for production of oil include species of *Nannochloris*, including *Nannochloropsis salina* or *Nannochloris oculata, Nannochloris atomus* Butcher, *Nannochloris maculata* Butcher, *Nannochloropsis gaditana* Lubian, and *Nannochloropsis oculata* (Droop), *Spirulina*, species of Chlorophyceae (this type of algae tends to produce more starch than lipids and has very high growth rates at 30° C. and high light in a water solution of type I at 55 mmho/cm), species of diatoms, diatom algae, Bacilliarophy, *Neochloris, Scenedesmus dimorphus, Euglena gracilis, Phaeodactylum tricornutum, Pleurochrysis carterae, Prymnesium parvum, Tetraselmis chui, Tetraselmis suecica, Isochrysis galbana*, species of *Botryococcus*, including but not limited to *Botryococcus braunii* (strain has been show to produce long chain hydrocarbons representing 86% of its dry weight), *Dunaliella tertiolecta* (a strain reported to have oil yield of about 37% (organic basis), *D. tertiolecta* (a fast growing strain with a high $CO_2$ sequestration rate). While certain green algae strains are very tolerant to temperature fluctuations, diatoms have a fairly narrow temperature range.

Embodiments of the present invention are adaptable to the production of either a single species or multiple species, in fresh, brackish, or saltwater. In specific embodiments of the current invention, cultivation is focused on a single species, for example for a freshwater finfish farm. However, system parameters are optimized through economies of scale in multi-species, multi-phyla farms. Therefore, other embodiments of multi-phyla farms depict more common uses of this invention. Thus, while the invention is particularly shown and described with references to illustrative embodiments thereof, it will be understood by those of ordinary skill in the art that various changes in form and details may be made therein (e.g., surrounding physical plant designs; water quality parameters, and feed species may differ) without departing from the scope of the invention.

In certain embodiments, the algae cultivated to produce biofuel may be genetically engineered (transgenic) to contain one or more isolated nucleic acid sequences that enhance oil production or provide other characteristics of use for algal culture, growth, harvesting or use. Methods of stably transforming algal species and compositions comprising isolated nucleic acids of use are well known in the art and any such methods and compositions may be used in the practice of the present invention. Exemplary transformation methods of use may include microprojectile bombardment, electroporation, protoplast fusion, PEG-mediated transformation, DNA-coated silicon carbide whiskers or use of viral mediated transformation (see, e.g., Sanford et al., 1993, Meth. Enzymol. 217:483-509; Dunahay et al., 1997, Meth. Molec. Biol. 62:503-9; U.S. Pat. Nos. 5,270,175; 5,661,017, incorporated herein by reference).

For example, U.S. Pat. No. 5,661,017 discloses methods for algal transformation of chlorophyll C-containing algae, such as the Bacillariophyceae, Chrysophyceae, Phaeophyceae, Xanthophyceae, Raphidophyceae, Prymnesiophyceae, Cryptophyceae, *Cyclotella, Navicula, Cylindrotheca, Phaeodactylum, Amphora, Chaetoceros, Nitzschia* or *Thalassiosira*. Compositions comprising nucleic acids of use, such as acetyl-CoA carboxylase, are also disclosed. U.S. Pat. No. 5,661,017 and all other patents and publications referenced in this application are hereby incorporated by reference.

In various embodiments, a selectable marker may be incorporated into an isolated nucleic acid or vector to select for transformed algae. Selectable markers of use may include neomycin phosphotransferase, aminoglycoside phosphotransferase, aminoglycoside acetyltransferase, chloramphenicol acetyl transferase, hygromycin B phosphotransferase, bleomycin binding protein, phosphinothricin acetyltransferase, bromoxynil nitrilase, glyphosate-resistant 5-enolpyruvylshikimate-3-phosphate synthase, cryptopleurine-resistant ribosomal protein S 14, emetine-resistant ribosomal protein S 14, sulfonylurea-resistant acetolactate synthase, imidazolinane-resistant acetolactate synthase, streptomycin-resistant 16S ribosomal RNA, spectinomycin-resistant 16S ribosomal RNA, erythromycin-resistant 23 S ribosomal RNA or methyl benzimidazole-resistant tubulin. Regulatory nucleic acid sequences to enhance expression of a transgene are known, such as *C. cryptica* acetyl-CoA carboxylase 5'-untranslated regulatory control sequence, a *C. cryptica* acetyl-CoA carboxylase 3'-untranslated regulatory control sequence, and combinations thereof.

Separation of Algae and Extraction of Oil

In various embodiments, algae may be separated from the water and various algal components, such as oil, may be extracted using any method known in the art. For example, algae may be partially separated from the water by sedimentation or any means known to one of ordinary skill in the art, or by processing using centrifuges, or even industrial scale commercial centrifuges of large volume capacity may be used to supplement or in place of other separation methods. Such centrifuges may be obtained from known commercial sources (e.g., Cimbria Sket or IBG Monforts, Germany; Alfa Laval AJS, Denmark). Centrifugation, sedimentation and/or filtering may also be of use to purify oil from other algal components. Separation of algae from the aqueous medium may be facilitated by addition of flocculants, such as clay (e.g., particle size less than 2 microns), aluminum sulfate or polyacrylamide. In the presence of flocculants, algae may be separated by simple gravitational settling, or may be more easily separated by centrifugation. Flocculent-based separation of algae is disclosed, for example, in U.S. Patent Appl. Publ. No. 20020079270, incorporated herein by reference.

The ordinarily skilled artisan will realize that any method known in the art for separating cells, such as algae, from liquid medium may be utilized. For example, U.S. Patent Appl. Publ. No. 20040121447 and U.S. Pat. No. 6,524,486, each incorporated herein by reference, disclose a tangential flow filter device and apparatus for partially separating algae from an aqueous medium. Other methods for algal separation from medium have been disclosed in U.S. Pat. Nos. 5,910,254 and 6,524,486, each incorporated herein by reference. Other published methods for algal separation and/or extraction may also be used. (See, e.g., Rose et al., Water Science and Technology 1992, 25:319-327; Smith et al., Northwest Science, 1968, 42:165-171; Moulton et al., Hydrobiologia 1990, 204/205:401-408; Borowitzka et al., Bulletin of Marine Science, 1990, 47:244-252; Honeycutt, Biotechnology and Bioengineering Symp. 1983, 13:567-575).

In various embodiments, algae may be disrupted to facilitate separation of oil and other components. Any method known for cell disruption may be utilized, such as ultrasonication, French press, osmotic shock, mechanical shear force, cold press, thermal shock, rotor-stator disruptors, valve-type processors, fixed geometry processors, nitrogen decompression or any other known method. High capacity commercial cell disruptors may be purchased from known sources. (E.g., GEA Niro Inc., Columbia, Md.; Constant Systems Ltd., Daventry, England; Microfluidics, Newton, Mass.) Methods for rupturing microalgae in aqueous suspension are disclosed, for example, in U.S. Pat. No. 6,000,551, incorporated herein by reference.

Conversion of Algae into Biodiesel

A variety of methods for conversion of photosynthetic derived materials into biodiesel are known in the art, and any such known method may be used in the practice of the instant invention. For example, the algae may be harvested, separated from the liquid medium, lysed and the oil content separated. The algal-produced oil will be rich in triglycerides. Such oils may be converted into biofuel using well-known methods, such as the Connemann process (see, e.g., U.S. Pat. No. 5,354,878, incorporated herein by reference). Standard transesterification processes involve an alkaline catalyzed transesterification reaction between the triglyceride and an alcohol, typically methanol. The fatty acids of the triglyceride are transferred to methanol, producing alkyl esters (biodiesel) and releasing glycerol. The glycerol is removed and may be used for other purposes.

Various embodiments involve use of the Connemann process (U.S. Pat. No. 5,354,878). In contrast to batch reaction methods (e.g., J. Am. Oil Soc. 61:343, 1984), the Connemann process utilizes continuous flow of the reaction mixture through reactor columns, in which the flow rate is lower than the sinking rate of glycerine. This results in the continuous separation of glycerine from the biodiesel. The reaction mixture may be processed through further reactor columns to complete the transesterification process. Residual methanol, glycerine, free fatty acids and catalyst may be removed by aqueous extraction. The Connemann process is well-established for production of biodiesel from plant sources, however the ordinarily skilled artisan will realize that any method known in the art for producing biofuels or biodiesel from triglyceride containing oils may be utilized, for example as disclosed in U.S. Pat. Nos. 4,695,411; 5,338,471; 5,730,029; 6,538,146; 6,960,672, each incorporated herein by reference.

Alternative methods that do not involve transesterification may also be used. For example, by pyrolysis, gasification, or thermochemical liquefaction (see, e.g., Dote, 1994, Fuel 73:12; Ginzburg, 1993, Renewable Energy 3:249-52; Benemann and Oswald, 1996, DOE/PC/93204-T5).

Other Algal Products

In certain embodiments, the disclosed methods, compositions and apparatus may be used for culture of animal or human-edible algae. For example, *Spirulina* is a planktonic blue-green algae that is rich in nutrients, such as protein, amino acids, vitamin B-12 and carotenoids. Human consumption of *Spirulina* grown in algae farms amounts to more than one thousand metric tons annually. The ordinarily skilled artisan will realize that any type of free-living algae may be grown, harvested and utilized by the claimed system, including edible algae like *Spirulina, Dunaliella* or *Tetraselmis* (see U.S. Pat. Nos. 6,156,561 and 6,986,323, each incorporated herein by reference.)

Other algal-based products may also be produced using the claimed methods, apparatus and system. For example, U.S. Pat. No. 5,250,427, incorporated herein by reference, discloses methods for photoconversion of organic materials such as algae into biologically-degradable plastics. Any such known method for producing useful products by culture of either normal or transgenic algae may be used.

EXAMPLES

Described here are some useful embodiments of the disclosed invention. The following examples are offered to illustrate, but do not limit the claimed invention. To better understand the utility of the present invention to one of ordinary skill in the art, some references include: Lewis III, et al. disclose a submersible raft for plant cultivation in U.S. Pat. No. 4,487,588; Hogen discloses a barrier grid structure and method of growing aquatic plants in U.S. Pat. No. 4,536,988, moorings and mooring design are discussed in Canada, R., Jr., and D. May. 1985. *Mooring developments and design philosophy at the national data buoy center*. OCEANS. Vol. 17; some methods of chemical liquification are disclosed in Dote, Y., S. Inoue, T. Ogi, and S. Yokoyama. 1996. Studies on the direct liquefaction of protein-contained biomass: The distribution of nitrogen in the products. *Biomass & Bioenergy* 11, (6): 491-8; additional techniques and construction in executing the floating pond of the present invention are disclosed in Gaylord, Edwin H., Charles N. Gaylord, and James E. Stallmeyer. 1997. *Structural engineering handbook*. 4th ed. New York: McGraw-Hill; an in-depth discussion of moorings that may be used with the present invention is in both Grosenbaugh articles Grosenbaugh, M. A. 1996. On the dynamics of oceanographic surface moorings. *Ocean Engineering* 23, (1) (JAN): 7-25; Grosenbaugh, M. A. 1995. Designing oceanographic surface moorings to withstand fatigue. *Journal of Atmospheric and Oceanic Technology* 12, (5) (OCT): 1101-10; nourishment and removal of unwanted gases such as $CO_2$ through algae is disclosed in Jones, I. S. F., and D. Otaegui. 1997. Photosynthetic greenhouse gas mitigation by ocean nourishment. *Energy Conversion and Management* 38, :S367-72; and also in Komori, S., T. Shimada, and Y. Murakami. 1995. Laboratory estimation of $CO_2$ transfer velocity across the air-sea interface. In *Biogeochemical processes and ocean flux in the western pacific*., eds. H. Sakai, Y. Nozaki, 69-81. Tokyo: TERRAPUB; liquefaction techniques that can be used with the present invention are disclosed in Matsui, T. O., A. Nishihara, C. Ueda, M. Ohtsuki, N. O. Ikenaga, and T. Suzuki. 1997. Liquefaction of micro-algae with iron catalyst. *Fuel* 76, (11) (SEP): 1043-8; other algae and methods that can be used with the present invention are disclosed in Minowa, T., and S. Sawayama. 1999. A novel microalgal system for energy production with nitrogen cycling. *Fuel* 78, (10) (AUG): 1213-5; Richmond, Amos, ed. 1986. *CRC handbook of microalgal mass culture*. Boca Raton, Fla.: CRC Press; a review of the U.S. Department of Energy's biodiesel study, providing many methods that can be used with the present invention, is provided in Sheehan, J., T. Dunahay, J. Benemann, and P. Roessler. 1998. *A look back at the U.S. department of Energy's aquatic species program: Biodiesel from algae*. NREL, TP-580-24190, each of which is hereby incorporated by reference.

Example 1

The rectangular floating pond in FIG. 8 is useful for testing system components and culture maintenance procedures. It has relatively small surface area coverage and is not submersible. A convenient pond size is 10 meters wide by 100 meters long. The size is chosen so that the ratio of the width of the pond compared to the diameter of the longitudinal member is large enough for a representative current to establish itself. If this ratio is O(1), then the longitudinal members provide too much shelter against the wind and the current will be negligible. Also, the ratio of wave heights to the diameter of the longitudinal member cannot be significantly more than 1, or the waves will swamp the pond. As such, the pond of this example is designed for surrounding waves with limited significant wave heights.

The buoyant framework can be made from many different materials like UV resistant PE, HD, MD, or LD, UV resistant PVC, or other such material. The list included here is for illustration purposes only and is non-limiting. It can also be composed of segments less than or equal to % the total length or width of the pond that are coupled during construction and decoupled during disassembly, as drawn in FIG. 3c. The pond depicted in FIG. 8 is well suited for testing the above mentioned materials and construction methods.

Likewise, the liner 146 can be made of a suitably strong and flexible material that is weather and puncture resistant such as HDPE, LDPE, PVC, PP, fabrics, and/or composites of these. The material can be made as cross-laminates, reinforced sheets, and/or multiply sheets. This list is for illustration purposes only and is non-limiting.

Recycling of the culture 148 from the downstream side to the upstream side enables simulation of much longer ponds. The pumps can be situated, for example, on a boat or buoy or on the buoyant framework, as long as their weights are counterbalanced as described with tube 144. Culture densities can be controlled by altering the ratio of recycled culture to make up water. During start up conditions, when algae concentrations are low, total recycle will be used. As an example, if the pond has an average depth of 20 cm and a current speed of 20 cm/s, then for a 10 m wide cultivation system the pump needs to be capable of pumping at least 20×1000×20 mL/s or approximately 6300 GPM. The culture can be grown starting with algae residing in the surrounding water or seeded with a specific algae mix. The pond is checked for algae concentration and concentrations of important nutrients like nitrogen, Fe, P, and others, and they are adjusted as needed. Other parameters like the pH and depth of the ponds can also be measured and controlled.

Algae from the pond can be used to test harvesting procedures and conversion of the algal biomass into other products like biofuels and direct or indirect food products, as described herein.

Example 2

The floating pond depicted in FIG. 8 can be converted to a submersible pond with some additional system components already described. Additional valving, piping, and optionally air pumping capabilities, so that the culture and surrounding water can be pumped into and out of longitudinal member 132, enable adjustment of the pond's buoyancy. If materials of construction for the framework result in an average density of the pond greater than the surrounding water with longitudinal member 132 filled, then longitudinal tubes filled with air, like tubes 44 in FIG. 4*b*, will have to be added. Addition of submerging lines and winches then enable adjusting the orientation of the pond and its equilibrium submersion depth.

Those of ordinary skill in the art will recognize many equivalents to the descriptions provided herein, using different materials, organisms, and parts for the framework, liner, culture, and mooring system. For example, the framework can be made of wood, different plastics such as HDPE, natural rubber, PP, PVC, different metals, etc. It can be made from barrels, pipes, tires, etc. The liner can be made of any material capable of forming a large flexible sheet impermeable to algae, like different plastics such as HDPE, LDPE, PP, PVC, etc. The mooring system can fasten to any fixed object such as a pier, quay, subsurface (seabed), land, or a floating object such as an anchor buoy, boat, floating platform, etc. All of the components can be constructed using commonly understood engineering principles, such as those found in Gaylord (1997). Additional components, as needed, like valves, pumps, winches, gauges, sensors, and other equipment can be added to the floating ponds described to enhance their operation.

What is claimed is:

1. A floating rectangular algae cultivation system with a length, a width, and ends designed for flotation and positioning on the surface of a body of water and wherein the positioning is for creation of a unidirectional longitudinal wind driven surface current of an algae culture within the system comprising:
   a. buoyant framework members comprising longitudinal members along the entire length and transverse members along the entire width with a set of two longitudinal and two transverse members forming all four of the ends of the system and at least one transverse member positioned between the two transverse members forming two of the ends of the system, wherein each buoyant framework member comprises:
      i. at least a first tube that is a ballast tube; and
      ii. additional tubes that are conduits for a plurality of process fluids selected from the group comprising nutrient feeds, culture, and surrounding water;
   b. an algae impermeable liner attached to the longitudinal members, wherein the buoyant framework and the liner create a containment area; and
   c. a mooring system.

2. An algae cultivation system according to claim 1 wherein the mooring system comprises a mooring line.

3. An algae cultivation system according to claim 1 wherein the mooring system comprises a buoy system.

4. An algae cultivation system according to claim 1 wherein the buoyant framework comprises at least one bundle of at least two tubes.

5. An algae cultivation system according to claim 1 wherein at least one of the longitudinal members connects to at least one of a ship, platform, buoy, floating tank, or a piping network.

6. An algae cultivation system according to claim 1 wherein the at least one transverse member positioned between the two transverse members forming two of the ends of the system further comprises one or more platforms.

7. An algae cultivation system according to claim 6 wherein the one or more platforms comprise one or more platform supports that float on top of the culture and are arranged to form lengthwise channels together with the liner.

8. An algae cultivation system according to claim 1 wherein the system is more than 1 kilometer long and more than 100 meters wide.

9. An algae cultivation system according to claim 1 which further comprises a submersion system for lowering the cultivation system below the surface of the body of water.

10. An algae cultivation system according to claim 9 wherein the submersion system comprises systems to change the buoyancy of the one or more first tubes.

11. An algae cultivation system according to claim 9 which further comprises an arced member designed to keep the system level while below the surface of the body of water.

12. An algae cultivation system according to claim 9 which further comprises a depth pressure sensor for controlling the depth of submersion of the algae cultivation system.

13. An algae cultivation system according to claim 9 wherein the submersion system comprises a winch system.

14. An algae cultivation system according to claim 13 wherein the winch system comprises a free hanging submerging line that extends to a subsurface.

15. An algae cultivation system according to claim 1 wherein there are at least two algae cultivation systems.

16. An algae cultivation system according to claim 1 wherein the cultivation system further comprises the process fluids.

17. An algae cultivation system according to claim 16 wherein the process fluids comprise a culture in the containment area.

18. An algae cultivation system according to claim 16 wherein the nutrient feeds include at least one selected from the group consisting of nitrogen, iron, and phosphorous.

19. An algae cultivation system designed for flotation and positioning on the surface of a body of water and wherein the positioning is for creation of a unidirectional longitudinal wind driven surface current of an algae culture within the system consisting of:
   a. comprising buoyant first and second perimeter longitudinal members spanning the length of the framework, and buoyant first and second perimeter transverse members spanning the width of framework and connecting the longitudinal members at their ends, and each of the buoyant first and second perimeter longitudinal members and the buoyant first and second perimeter transverse members comprises: i. at least a first tube that is a ballast tube; and ii. additional tubes that are conduits for a plurality of process fluids selected from the group comprising nutrient feeds, culture, and surrounding water;
      i. the two perimeter longitudinal members are on opposing sides of the framework;
      ii. the two perimeter transverse members are on opposing sides forming an upstream end and a downstream end of the framework and single containment area; and
      iii. there is at least one intersecting transverse member positioned parallel to and in-between the two perimeter transverse members in the single containment area and connecting to the first and second perimeter longitudinal members wherein each of the at least one intersecting transverse member is positioned in spaced relationship to the surface of the water in the containment area such that wherein there is a recirculating pump at the second perimeter transverse member, which pumps algae culture arriving at the second perimeter transverse member back to the first perimeter transverse member to maintain a surface current in the containment area;
   b. an algae impermeable liner attached to the framework, wherein the framework and the liner create the single containment area and the at least one intersecting transverse member is positioned in the single containment area and wherein the unidirectional longitudinal wind driven surface current of an algae culture can travel between the upstream and downstream end in the single containment area;
   c. an algae culture contained in the single containment area;
   d. a mooring system for positioning the system in the wind; and
   e. two or more culture harvesting and nutrient replenishment systems, wherein at least one harvesting and nutrient system is positioned on an intersecting transverse member.

20. A floating rectangular algae cultivation system with a length, a width, and ends comprising:
   a. buoyant framework members comprising longitudinal members along the entire length and transverse members along the entire width with a set of two longitudinal and two transverse members forming all four of the ends of the system and at least one transverse member positioned between the two transverse members forming two of the ends of the system, wherein each buoyant framework member comprises:
      i. at least one first tube that is a ballast tube; and
      ii. additional tubes that are conduits for a plurality of process fluids selected from the group comprising nutrient feeds, culture, and surrounding water;
   b. an algae impermeable liner attached to the longitudinal members, wherein the buoyant framework and the liner create a containment area; and
   c. a mooring system,
   wherein the at least one transverse member positioned between the two transverse members forming two of the ends of the system comprises one or more platforms that comprise one or more platform supports that float on top of the culture and are arranged to form lengthwise channels together with the liner.

21. A floating rectangular algae cultivation system with a length, a width, and ends designed for flotation and positioning on the surface of a body of water and wherein the positioning is for creation of a unidirectional longitudinal wind driven surface current of an algae culture within the system comprising:
   a. a buoyant framework arranged into longitudinal members along the entire length and transverse members along the entire width with a set of two longitudinal and two transverse members forming all four of the ends and at least one transverse member positioned between the set of two transverse members forming two of the ends, and each of the member comprises: i. at least a first pipe that is a ballast tube; and ii. additional pipes that are conduits for a plurality of process fluids selected from the group comprising nutrient feeds, culture, and surrounding water;
   b. an algae impermeable liner attached to the longitudinal members, wherein the buoyant framework and the liner create a containment area;
   c. a mooring system; and
   d. culture harvesting and nutrient replenishment systems positioned at the at least one transverse member positioned between the set of two transverse members forming two of the ends.

22. An algae cultivation system according to claim 21 wherein the mooring system comprises a mooring line.

23. An algae cultivation system according to claim 21 wherein the mooring system comprises a buoy system.

24. An algae cultivation system according to claim 21 wherein the longitudinal members comprise at least one bundle of at least two pipes.

25. An algae cultivation system according to claim 24 wherein the bundle comprises at least two pipes, a first pipe to pump in process fluids to the containment area and a second pipe to pump out process fluids from the containment area.

26. An algae cultivation system according to claim 21 wherein at least one of the longitudinal members connects to at least one of a ship, platform, buoy, floating tank, or a piping network.

27. An algae cultivation system according to claim 21 wherein the system is more than 1 kilometer long and more than 100 meters wide.

28. An algae cultivation system according to claim 21 wherein there are at least two algae cultivation systems.

29. An algae cultivation system according to claim 21 which further comprises a submersion system for lowering the cultivation system below the surface of the body of water.

30. An algae cultivation system according to claim 29 wherein the longitudinal members comprise at least one bundle of at least two pipes and at least one of the pipes is a ballast tube.

31. An algae cultivation system according to claim 30 wherein the submersion system comprises systems to change the buoyancy of the ballast tube.

32. An algae cultivation system according to claim 31 which further comprises an arced member designed to keep the system level while below the surface of the body of water.

33. An algae cultivation system according to claim 31 which further comprises a depth pressure sensor for controlling the depth of submersion of the algae cultivation system.

34. An algae cultivation system according to claim 31 wherein the submersion system comprises a winch system.

35. An algae cultivation system according to claim 34 wherein the winch system comprises a free hanging submerging line that extends to a subsurface.

36. An algae cultivation system according to claim 21 wherein the at least one transverse member positioned between the two transverse members forming two of the ends of the system further comprises one or more platforms.

37. An algae cultivation system according to claim 36 wherein the one or more platforms comprise one or more platform supports that float on top of the culture and are arranged to form lengthwise channels together with the liner.

38. An algae cultivation system according to claim 21 wherein the cultivation system further comprises the process fluids.

39. An algae cultivation system according to claim 38 wherein the nutrient feeds include at least one selected from the group consisting of nitrogen, iron, and phosphorous.

40. An algae cultivation system according to claim 38 wherein the process fluids comprise a culture in the containment area.

41. A floating rectangular algae cultivation system with a length, a width, and ends designed for flotation and positioning on the surface of a body of water and wherein the positioning is for creation of a unidirectional longitudinal wind driven surface current of an algae culture within the system comprising:

a. a buoyant framework arranged into longitudinal members along the entire length and transverse members along the entire width with a set of two longitudinal and two transverse members forming all four of the ends and at least one transverse member positioned between the set of two transverse members forming two of the ends, and each of the member comprises: i. at least a first pipe that is a ballast tube; and ii. additional pipes that are conduits for a plurality of process fluids selected from the group comprising nutrient feeds, culture, and surrounding water;

b. an algae impermeable liner attached to the longitudinal members, wherein the buoyant framework and the liner create a containment area;

c. a mooring system; and d. culture harvesting and nutrient replenishment systems positioned at the at least one transverse member positioned between the set of two transverse members forming two of the ends, wherein the at least one transverse member positioned between the two transverse members forming two of the ends of the system comprises one or more platforms that comprise one or more platform supports that float on top of the culture and are arranged to form lengthwise channels together with the liner.

42. A floating rectangular algae cultivation system with a length, a width, and ends designed for flotation and positioning on the surface of a body of water and wherein the positioning is for creation of a unidirectional longitudinal wind driven surface current of an algae culture within the system comprising:

a. a buoyant framework arranged into longitudinal members along the entire length and transverse members along the entire width with a set of two longitudinal and two transverse members forming all four of the ends and at least one transverse member positioned between the set of two transverse members forming two of the ends, and each of the member comprises: i. at least a first pipe that is a ballast tube; and ii. additional pipes that are conduits for a plurality of process fluids selected from the group comprising nutrient feeds, culture, and surrounding water;

b. an algae impermeable liner attached to the longitudinal members, wherein the buoyant framework and the liner create a containment area;

c. a mooring system; and d. at least one of culture harvesting and nutrient replenishment systems positioned at each of the two transverse members forming two of the ends and at the at least one transverse member positioned between the set of two transverse members forming two of the ends.

\* \* \* \* \*